(12) United States Patent
Casalino et al.

(10) Patent No.: US 12,318,622 B2
(45) Date of Patent: Jun. 3, 2025

(54) APPARATUS AND METHOD FOR FAT AND CELLULITE REDUCTION USING RF ENERGY IN COMBINATION WITH MAGNETIC MUSCLE THERMOSTIMULATION (EMS)

(71) Applicant: BIOS S.R.L., Milan (IT)

(72) Inventors: Lorenzo Casalino, Milan (IT); Aldo Casalino, Milan (IT)

(73) Assignee: BIOS SRL, Milan (IT)

( * ) Notice: Subject to any disclaimer, the term of this patent is extended or adjusted under 35 U.S.C. 154(b) by 595 days.

(21) Appl. No.: 17/670,872

(22) Filed: Feb. 14, 2022

(65) Prior Publication Data

US 2022/0226662 A1    Jul. 21, 2022

Related U.S. Application Data

(63) Continuation of application No. 17/315,297, filed on May 8, 2021, now Pat. No. 11,278,732, which is a
(Continued)

(51) Int. Cl.
*A61N 2/00* (2006.01)
*A61M 37/00* (2006.01)
(Continued)

(52) U.S. Cl.
CPC ............. *A61N 2/002* (2013.01); *A61M 37/00* (2013.01); *A61N 1/08* (2013.01); *A61N 1/403* (2013.01);
(Continued)

(58) Field of Classification Search
CPC .......... A61N 2/002; A61N 1/08; A61N 1/403; A61N 2/004; A61N 2/02; A61N 2001/083;
(Continued)

(56) References Cited

U.S. PATENT DOCUMENTS

| 2011/0021863 | A1  | 1/2011 | Burnett et al. |
| 2014/0249355 | A1* | 9/2014 | Martinez ................ A61N 2/004 600/14 |

(Continued)

FOREIGN PATENT DOCUMENTS

| KR | 10-2006-0134050 | 12/2006 |
| KR | 10-2007-0108191 | 11/2007 |

(Continued)

OTHER PUBLICATIONS

Search Report—corresponding PCT Application No. PCT/IB2020/051700, dated May 20, 2020, 4 pages.

*Primary Examiner* — Carrie R Dorna
*Assistant Examiner* — Joshua Daryl D Lannu
(74) *Attorney, Agent, or Firm* — ISUS INTELLECTUAL PROPERTY PLLC; Anthony Jason Mirabito

(57) ABSTRACT

A system for cosmetically treating a patient's skin or body with one or more EMS coils and/or RF electrodes mounted on a planar holder; a hydrogel containing gel pad, the gel pad being positionable between the holder and the skin tissue; wherein the gel pad being of a material that is biocompatible and conducts RF and/or EMS energy when EMS energy is applied from the one or more EMS coils; a programmable controller to activate the one or more EMS coils; the programmable controller, after the planar holder is applied to the skin tissue, being configured to activate one or more of the plurality of EMS coils to provide treatment in the form of stimulation to the skin tissue.

6 Claims, 22 Drawing Sheets

Related U.S. Application Data continuation of application No. PCT/IB2020/051700, filed on Feb. 27, 2020.

(60) Provisional application No. 62/908,741, filed on Oct. 1, 2019, provisional application No. 62/884,099, filed on Aug. 7, 2019, provisional application No. 62/812,123, filed on Feb. 28, 2019.

(51) Int. Cl.
| | | |
|---|---|---|
| *A61N 1/04* | (2006.01) | |
| *A61N 1/08* | (2006.01) | |
| *A61N 1/32* | (2006.01) | |
| *A61N 1/40* | (2006.01) | |
| *A61N 2/02* | (2006.01) | |

(52) U.S. Cl.
CPC ............ *A61N 2/004* (2013.01); *A61N 2/02* (2013.01); *A61M 2037/0007* (2013.01); *A61N 2001/083* (2013.01)

(58) Field of Classification Search
CPC .... A61N 2/006; A61N 1/0412; A61N 1/0496; A61N 1/328; A61M 37/00; A61M 2037/0007
See application file for complete search history.

(56) References Cited

U.S. PATENT DOCUMENTS

| | | | |
|---|---|---|---|
| 2015/0032178 A1* | 1/2015 | Simon | ................ A61N 1/36025 607/45 |
| 2015/0157873 A1 | 6/2015 | Sokolowski | |
| 2018/0000533 A1 | 1/2018 | Boll et al. | |
| 2018/0001107 A1* | 1/2018 | Schwarz | ................ A61N 2/004 |

FOREIGN PATENT DOCUMENTS

| | | |
|---|---|---|
| KR | 10-2012-0116934 | 10/2012 |
| KR | 10-1472983 | 12/2014 |
| KR | 10-2015-0002463 | 1/2015 |
| KR | 10-2015-0105065 | 9/2015 |
| KR | 10-2015-0135335 | 12/2015 |
| WO | 2011055282 | 5/2011 |
| WO | 2012001643 | 1/2012 |

* cited by examiner

APPARATUS AND METHOD FOR FAT AND CELLULITE REDUCTION USING RF ENERGY IN COMBINATION WITH MAGNETIC MUSCLE THERMOSTIMULATION (EMS)

RELATED APPLICATIONS

This application is a continuation application of U.S. application Ser. No. 17/315,297, filed May 8, 2021, which is a continuation application of PCT/IB2020/051700, filed Feb. 27, 2020, which is related to U.S. Provisional Application No. 62/812,123, filed Feb. 28, 2019, U.S. Provisional Application No. 62/884,099, filed Aug. 7, 2019, and U.S. Provisional Application No. 62/908,741, filed Oct. 1, 2019, the entire contents of each of which are herein incorporated by reference, and to which priority is claimed as to each.

FIELD OF THE INVENTION

The present invention relates to apparatus and methods for the treatment and reduction of adipose tissue, cellulite and tissue irregularities (such as wrinkles) in a human body using radiofrequency energy (RF) and/or electromagnetic muscle stimulation (EMS).

BACKGROUND OF THE PRESENT INVENTION

Devices and methods are known in the industry which are designed to treat (read reduce) adipose tissue in humans. Some of these employ laser energy to essentially melt away the fat cells, other devices utilize cold temperatures around 0 to 5 degrees C. to cause the freezing and destruction of fat cells, and still other devices use RF energy which is targeted to the layer of the fat cells to heat the cells and cause them to melt and then be drained away by the body's internal systems.

It is to the very latter of these technologies that the present invention is directed, in which RF energy is employed to provide more effective treatment over larger areas of the body to reduce treatment duration. By treating larger areas of the body during a single procedure, overheating of the epidermis is avoided and the total treatment time is reduced.

In addition, one of the issues that an operator may encounter is a necessity of holding the handpiece that provides the treatment energy to the patient's skin tissue during the treatment, thus requiring the operator (unnecessarily) to be occupied holding the device during the treatment.

Also, a known problem with energy generating devices, such as radiofrequency (RF) generating devices is that, when applied to skin tissue, the RF energy may produce hotspots so that one portion of the skin tissue is treated differently than other portions of the skin tissue.

While various radiofrequency electrodes are known and used, one problem encountered in using radiofrequency devices in the skin treatment is that the shape and size of the electrode or electrodes may well affect the amount of energy that is imparted to the skin tissue. Obviously, it is desirable that the energy provided to the skin tissue be uniform across the entire area affected by the radiofrequency electrode or electrodes.

In known devices employing radiofrequency technology, it is typical to manually set a selected frequency at which the radiofrequency energy is imparted. This may have certain disadvantages in providing a thorough treatment of the skin tissue through different depths of the skin tissue anatomy.

While it may be known to provide a matrix of radiofrequency electrodes in a single unit or housing, it is important that the individual electrodes in the matrix be controlled in a manner to provide the most efficacious treatment to the skin tissue, and, obviously, if the matrix of RF electrodes could be controlled automatically the results would be less operator time spent on a particular treatment as well as a more effective treatment of skin tissue treatment conditions.

One consequence of applying radiofrequency or any other kind of energy to the skin tissue is that of generating heat and thus causing skin tissue heating. In particular, excessive heating of the epidermis is one aim to be avoided so that there is not discomfort or pain on the part of the patient. Some systems avoid or at least attempt to avoid pain by providing the radiofrequency treatment only sporadically or at given times for given periods, as in a pulsed manner. With the desire that the treatment, be given on more or less continuous basis so that thorough treatment may be had as well as shortening the total amount of treatment, it may be useful to provide cooling of the epidermis.

Other known devices use systems to cool the skin that is under the RF electrodes, such as the provision of passages of a coolant in the electrode, or electronic devices (such as fans or even Peltier cells). However, this solution does not allow the temperature sensor placed between the electrode and the skin to correctly measure the skin temperature. Not knowing the temperature of the skin issue, the operator may be unable to know what is be the temperature inside the tissues in depth, for example in the fat, and thus this in turn impairs the overall efficacy of the treatment.

If the aim of the radiofrequency treatment is to reduce adipose tissue (fat) content deep in the skin tissue, the regimen of applying radiofrequency energy may well be different from the regimen of applying radiofrequency energy if the desire is to eliminate or reduce wrinkles in parts of the skin tissue that are located above the level of adipose tissue. Thus, if a device or technique can be developed to identify where, for example, the selected tissue lies within the skin tissue, then treatment can be adjusted automatically so that the desired level of radiofrequency treatment may be initiated.

In those instances of treatment in which the treatment device may be moved over the body portions of the skin tissue, it is obviously desirable that each portion of the skin tissue desired to be treated is actually treated, but also it may be important that portions of the skin tissue not be over-treated by the device being repeatedly placed over the same area tissue that had previously been treated.

In other radiofrequency devices, it is common that the radiofrequency be provided as one or more radiofrequency energy pulses. While this may be done in order to control the heating of the underlying skin tissue, discontinuities between pulses may not make the treatment regime as efficient as it could be. It may be that a regime in which the radiofrequency energy is provided on a more or less continuous basis and perhaps even over different frequencies may have the result of more thorough treatment.

It is to overcome one or more the disadvantages of present systems identified above that the present invention is addressed and described in the following detailed description of the present invention.

SUMMARY OF THE PRESENT INVENTION

In an aspect, a method for cosmetically treating a patient's skin tissue includes: providing a plurality of RF electrodes mounted on a cooled silicone planar holder; providing a programmable controller to activate one or more of the plurality of electrodes; the method includes the steps of: a. applying the planar holder to the skin tissue; b. securing the planar holder to the patient; c. activating one or more of the plurality of RF electrodes one of individually, sequentially, or simultaneously in a continuous manner to provide treatment; d. selecting one or more frequencies in a scan mode for application by the one or more of the plurality of RF electrodes; thereby the skin tissue underlying the one or more RF electrodes is selectively treated by activation or one or more of the plurality of RF electrodes at one or more selected frequencies in a continuous manner.

In another aspect, the planar holder further comprises a cooling device for maintaining a constant skin tissue temperature when the one or more of the plurality of RF electrodes is activated using sensors that measure the skin tissue temperature in areas surrounding the plurality of RF electrodes. The cooling device may include one or more of: one or more Peltier elements, one or more fan devices that implement air cooling, or circulating cooling fluids. Further, the one or more electrodes may comprise a plurality of electrodes arranged in a matrix. The cooling device may be mounted centrally within the matrix of RF electrodes.

In an aspect, a console includes a programmable controller and a user interface, the console being operable to control the activation of the one or more plurality of RF electrodes mounted on the planar holder. The holder further may include one or more skin temperature sensors, and wherein the one or more temperature sensors transmit skin temperature measurements to the programmable controller. The holder may further comprise one or more impedance measurement circuits, and wherein the one or more impedance circuits transmit skin impedance measurements to the programmable controller. The programmable controller may activate the one or more of the plurality of RF electrodes in response to the sensed transmitted impedance measurements, and the controller may vary the RF electrode frequency selected in response to the sensed transmitted impedance measurements. The frequencies selected may be one or more of: 0.475 MHz, 1.0 MHz, 2.0 MHz, 4.0 MHz and 6.0 MHz (+/−20%) and may be selected one of: individually or in a scan mode. The planar holder may further comprise a securing belt to secure the planar holder to the patient's skin tissue, as well as the planar holder may have two sides, one side being a thermally conducting silicone rubber material to contact the skin tissue and the second side being of a non-thermally conducting material. The plurality of electrodes may be removably mounted on the planar holder. The electrodes may be mounted in the planar holder such that on the side of the holder that contacts the skin tissue, the plurality of RF electrodes is spaced from and are not in contact with the skin tissue. The method may include the step of applying a solid gel plate between the electrodes and the skin, and wherein the solid gel plate is preferably of an adhesive material that is biocompatible and conducts RF energy.

In an aspect, a system for cosmetically treating a patient's skin tissue includes: a plurality of RF electrodes mounted on a cooled silicone planar holder; a programmable controller to activate one or more of the plurality of electrodes; the programmable controller, after the planar holder is applied to and secured to the skin tissue, being configured to activate one or more of the plurality of RF electrodes in a continuous manner to provide treatment in a scan mode at one or more frequencies for application by the one or more of the plurality of RF electrodes; thereby, the skin tissue underlying the one or more RF electrodes is selectively treated by activation or one or more of the plurality of RF electrodes at one or more selected frequencies in a continuous manner.

In a further aspect, a system for cosmetically treating a patient's skin tissue and transdermally delivering substances into the skin tissue, includes a plurality of RF electrodes mounted on a silicone planar holder; a hydrogel containing gel pad positionable between the holder and the skin tissue; the gel pad including materials for transdermal delivery into the skin tissue; the gel pad being of a material that is biocompatible and conducts RF energy; a programmable controller to activate one or more of the plurality of electrodes. The programmable controller, after the planar holder is applied to and secured to the skin tissue, being configured to activate one or more of the plurality of RF electrodes in a continuous manner to provide treatment in a scan mode at one or more frequencies for application by the one or more of the plurality of RF electrodes. Thereby, the skin tissue underlying the one or more RF electrodes is selectively treated by activation or one or more of the plurality of RF electrodes at one or more selected frequencies in a continuous manner; and, whereby the one or more RF electrodes when activated generate heat in the skin tissue, the heat generated causing the materials within the gel pad to be transdermally delivered into the skin tissue at a predetermined temperature. The materials for transdermal delivery are selected from: pharmaceutical materials, cosmetic materials, and time release materials. Further, the planar holder further comprises a cooling device for maintaining a constant skin tissue temperature when the one or more of the plurality of RF electrodes is activated using sensors that measure the skin tissue temperature in areas surrounding the plurality of RF electrodes. The system may further comprise a console, the console including the programmable controller and a user interface, the console being operable to control the activation of the one or more plurality of RF electrodes mounted on the planar holder. The planar holder may have two sides, one side being a thermally conducting silicone rubber material to contact the skin tissue and the second side being of a non-thermally conducting material. The plurality of electrodes may be removably mounted on the planar holder. The electrodes may be mounted in the planar holder such that on the side of the holder that contacts the skin tissue, the plurality of RF electrodes is spaced from and are not in contact with the skin tissue.

In a further aspect, one or more EMS coils may be mounted on the planar holder, the one or more EMS coils being mounted in the vicinity of the center position on the planar holder. The programmable controller may be configured to activate the plurality of RF electrodes and the one or more EMS coils one or more of: simultaneously or sequentially.

In yet another aspect, a system for cosmetically treating a patient's skin tissue includes a plurality of RF electrodes mounted on a silicone planar holder; one or more EMS coils mounted on the silicon planar holder; a programmable controller to activate one or more of the plurality of electrodes and the one or more EMS coils; the programmable controller, after the planar holder is applied to and secured to the skin tissue, being configured to activate one or more of the plurality of RF electrodes in a continuous manner to provide treatment in a scan mode at one or more frequencies for application by the one or more of the plurality of RF electrodes; the programmable controller further being configured to activate the one or more EMS coils; whereby the skin tissue underlying the one or more RF electrodes is selectively treated by activation or one or more of the plurality of RF electrodes at one or more selected frequencies in a continuous manner and by the one or more EMS coils; and, whereby the one or more RF electrodes when activated generate heat in the skin tissue and the one or more EMS coils provide stimulation to the skin tissue. The one or more EMS coils may be mounted in the vicinity of the center position on the planar holder. The plurality of RF electrodes number one of: 1 or 4. The programmable controller is configured to activate the plurality of RF electrodes and the one or more EMS coils one or more of: simultaneously or sequentially.

In yet a further aspect, a method for cosmetically treating a patient's skin tissue and transdermally delivering substances into the skin tissue includes: providing a plurality of RF electrodes mounted on a silicone planar holder; providing a hydrogel containing gel pad positionable between the holder and the skin tissue; wherein the gel pad including materials for transdermal delivery into the skin tissue; the gel pad being of a material that is biocompatible and conducts RF energy; providing a programmable controller to activate one or more of the plurality of electrodes; applying and securing the planar holder to the skin tissue surface; the programmable controller, after the planar holder is applied to and secured to the skin tissue surface, activating one or more of the plurality of RF electrodes in a continuous manner to provide treatment in a scan mode at one or more frequencies for application by the one or more of the plurality of RF electrodes; whereby the skin tissue underlying the one or more RF electrodes is selectively treated by activation or one or more of the plurality of RF electrodes at one or more selected frequencies in a continuous manner; and, whereby the one or more RF electrodes when activated generate heat in the skin tissue, the heat generated causing the materials within the gel pad to be transdermally delivered into the skin tissue at a predetermined temperature.

In an aspect, a method for cosmetically treating a patient's skin tissue comprises: providing a plurality of RF electrodes mounted on a silicone planar holder; providing one or more EMS coils mounted on the silicon planar holder; providing a programmable controller to activate one or more of the plurality of electrodes and the one or more EMS coils; applying and optionally securing the planar holder to the skin tissue; the programmable controller, after the planar holder is applied to and secured to the skin tissue, activating one or more of the plurality of RF electrodes in a continuous manner to provide treatment in a scan mode at one or more frequencies for application by the one or more of the plurality of RF electrodes; the programmable controller further being configured to activate the one or more EMS coils; whereby the skin tissue underlying the one or more RF electrodes is selectively treated by activation of one or more of the plurality of RF electrodes at one or more selected frequencies in a continuous manner and by the one or more EMS coils; and, whereby the one or more RF electrodes when activated generate heat in the skin tissue and the one or more EMS coils provide stimulation to the skin tissue. The stimulation type from EMS coils is in the form of muscle contractions due to the sudden and intense variations in the magnetic field induced onto the muscles.

In a further aspect, a system for cosmetically treating a patient's skin tissue, comprises:
one or more EMS coils mounted on a planar holder; a hydrogel containing gel pad, the gel pad being positionable between the holder and the skin tissue; wherein the gel pad being of a material that is biocompatible and conducts EMS energy when EMS energy is applied from the one or more EMS coils; a programmable controller to activate the one or more EMS coils; the programmable controller, after the planar holder is applied to the skin tissue, being configured to activate one or more of the plurality of EMS coils to provide treatment in the form of stimulation to the skin tissue.

In yet another aspect, a method of cosmetically treating a patient's skin tissue, comprises: providing one or more EMS coils mounted on a planar holder; providing a hydrogel containing gel pad, the gel pad being positionable between the holder and the skin tissue; positioning the gel pad between the holder and the skin tissue; wherein the gel pad being of a material that is biocompatible and conducts EMS energy when EMS energy is applied from the one or more EMS coils; providing a programmable controller to activate the one or more EMS coils; the programmable controller, after the planar holder is applied to the skin tissue, activating one or more of the plurality of EMS coils to provide treatment in the form of stimulation to the skin tissue which may be, as mentioned, in the form of muscle contractions due to the sudden and intense variations of the magnetic field induced on the muscles. The gel pad may underlie both the RF electrodes and the EMS coils or may underlie just the RF electrodes or just the EMS coil(s).

In an aspect, the method further comprises the step of securing the planar holder to the skin tissue. The step of securing the planar holder to the skin tissue may be through one of a belt or an adhesive. The method may include an accelerometer, and further comprising the steps of setting the most suitable parameters to obtain the best performing muscle contractions. Further, the method may include the step of positioning the gel pad under the RF electrodes, or under the EMS coil, or under both.

DETAILED DESCRIPTION OF THE PRESENT INVENTION

A First Embodiment: Structure of an RF Energy Device

Figure 1A:
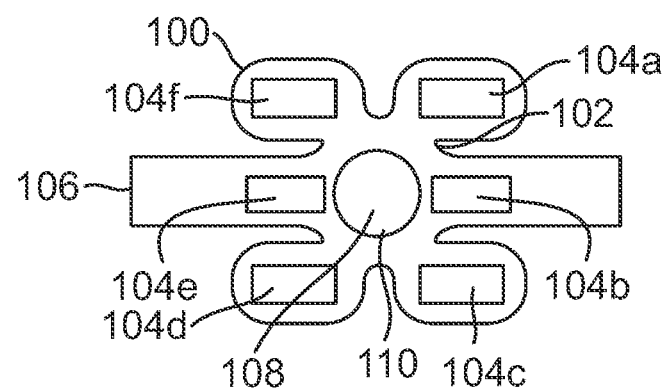
FIGS. 1A through 1C illustrate one embodiment of a RF energy applicator of the present invention.
Figure 1B:
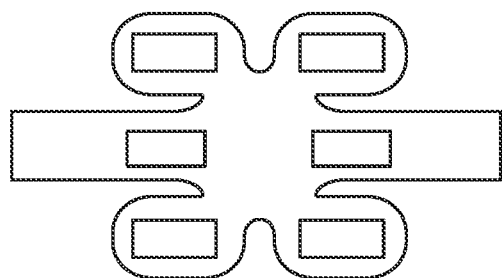
Figure 1C:
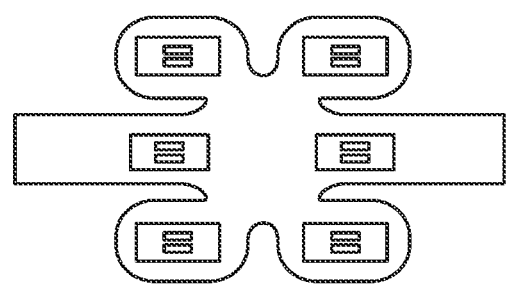

Turning now to FIGS. 1A through 1C, these figures show a first embodiment of the present invention. The device, numbered as 100, may be referred to as herein a radiofrequency belt. The belt 100 includes a planar holder body 102 which may be made from thermally conductive silicone rubber, plastic or any other known non-electro-conductive material.

Mounted on the holder body 102 are a number of radiofrequency electrodes. While in FIG. 1A there is shown six such radiofrequency electrodes, 104a-104f, it is to be understood that a number less or more may be implemented in mounted on the holder body 102. In order to maintain the holder device 102 stationary and mounted on a patient's body, a belt 106 attached to the body 102 may be implemented. The belt 106 may wrap around a body portion such as torso or the leg or the arms or the chin or the cheeks, and may include a conventional latching mechanism such as a Velcro. An adhesive material may also be utilized. The holder body 102 also may include a Peltier-type solid state cooler 108 shown mounted centrally to the array of electrodes 104a to 104f, but may be placed in other positions on body 102. In addition, multiple Peltier coolers may be implemented and mounted on the body 102. A suitable cable 110 is shown connected to the body 102 and may be used to connect with a suitable known console which would supply electrical power for the Peltier cooler 108 and provide power to the electrodes 104a through 104f. One purpose of the Peltier cell, applied to the belt, is to cool the skin under the electrodes, but, through the planar holder thermally conductive silicone rubber, to in addition maintain a constant temperature (28° C. for example) across the entire skin area that is around the electrodes.

FIG. 1C illustrates the holder 102 but without the RF electrodes mounted within it, to be described below in connection with FIG. 2. FIG. 1B illustrates the holder 102 from the bottom side, that is, the side which places the electrodes in the vicinity of the skin tissue.

The holder 102 as mentioned may preferably be made of silicon rubber or some other material which has a high thermal conductivity on the side it will be in contact with the skin while being thermally insulated on the other side. It is known that silicone is biocompatible and is easily sterilize or disinfected, but several other high thermal conductivity materials also could be used.

In addition, the holder 102 may include one or more temperature sensors to monitor temperature and transmit those temperatures to a programmable controller mounted in the console to provide the relative average temperature of the areas of the of skin tissue in and around the radiofrequency electrodes. The sensors, which may be positioned at selected and multiple points on the silicone rubber holder 102, may detect the skin temperature under the electrodes but preferably only that of the skin around the electrodes.

Other temperature sensors may be mounted on the inside of the radiofrequency electrodes themselves in order to be able to detect temperature of the electrodes and to send that information as necessary or desired to the console.

The controller is able in this way to detect the temperature difference between the one detected under the skin and the average temperature detected on the skin around the area treated by the electrodes. By having this information, the controller can be programmed to increase or decrease the temperature of the skin around the electrodes, reducing the pain or discomfort of the patient.

It also may be desirable that the radiofrequency electrodes be easily removed from the holder 102 in the event that it becomes necessary to clean the electrodes or one or more of the electrodes becomes defective or to simply allow an operator to change the number of electrodes desired to provide a particular type of treatment.

Peltier coolers, if employed, will, of course, generate heat on the side of the cell not in contact with the skin tissue and it may be necessary to actively cool and withdraw that heat away from the cell. This may be done by air circulation means or may be accomplished by liquid cooling in which the device of FIG. 1A may be modified to include water lines that provide cooling water or other fluid to or to the vicinity of Peltier coolers to withdraw heat and dispose of the heat generated.

Figure 2:
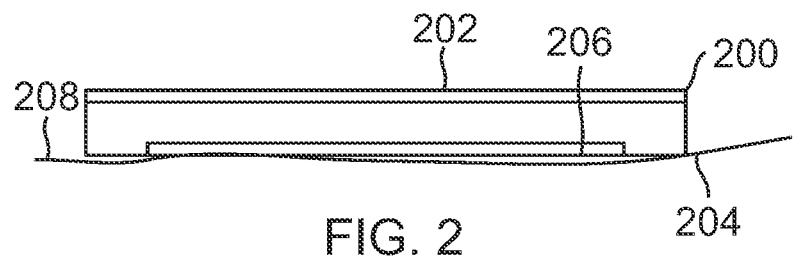
FIG. 2 illustrates one embodiment of the structure of RF electrodes in connection with the embodiment of FIGS. 1A though 1C.

Turning now to FIG. 2, this figure illustrates in a side view details of the electrode structure and the electrode mounting on the holder 102. Holder 200 includes a ledge 204 which surrounds the electrode 202 and holds it in place. As mentioned above, due to the construction of the holder 200, the electrodes may be removed and/or replaced. The ledge 204 prevents the electrode from falling through the holder 200, but as well provides a standoff from the skin tissue 208 so that the electrode does not come into contact directly with the skin tissue 208. A uniform conductive RF hydrogel plate 206 may be inserted or otherwise positioned within the holder 200. With this arrangement, the edge of the electrode does not come into contact with the skin. It is known in the relevant art that RF energy emitted by electrodes thickens on the edges, both if the electrodes are circular in shape, but especially if they are rectangular. The concentration of energy on the edges can create burns to the skin, and to avoid this, the operator is forced to shorten the duration of the treatment or to not exceed temperature levels higher than 42-44 degrees C.

The electrode 202 may be constructed in a manner to include an outer housing that contains the active device which produces the radiofrequency energy. The active device may not occupy the entire interior of the electrode 202, and the remainder of the interior of the electrode housing 202 may be filled with a suitable grease, oil or thermal gel which has the function of homogenizing the heating of the electrode 202 so that across electrode 202 uniform heating and energy is imparted to the skin tissue. This arrangement may also reduce "hot spots" and heating differential across the extent of the electrode. FIG. 5 illustrates an enlarged view of a RF electrode, in this case a circular electrode, containing a thermal gel or grease.

Figure 5A:
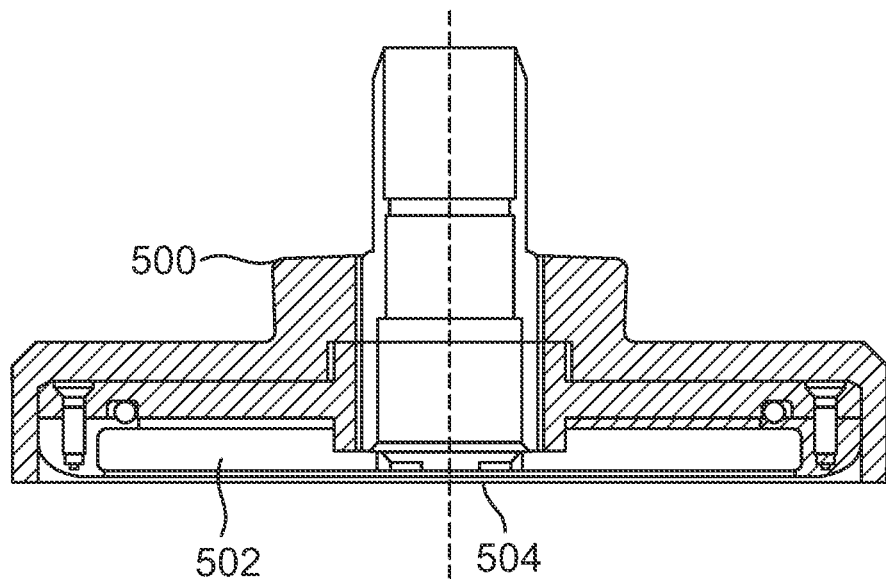
FIGS. 5A-5C illustrate a RF electrode filled with a thermal gel-type material.
Figure 5B:
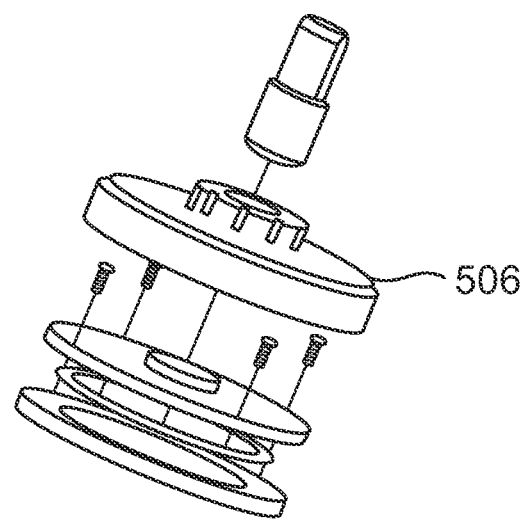
Figure 5C:
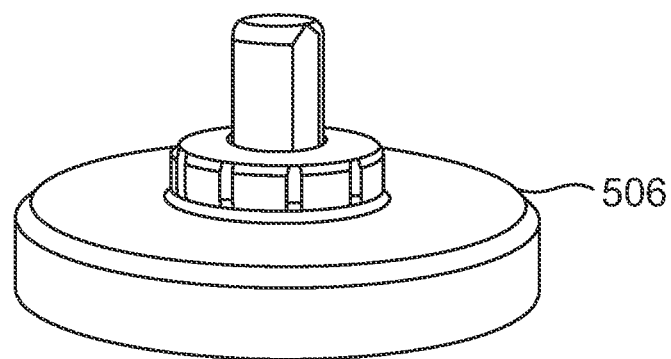

As shown in FIG. 5A, a circular electrode assembly 500 includes a volume 502 for containing thermal grease or gel, a temperature sensor 504, all assembled within the housing 500. FIG. 5B shows an exploded view of the RF circular electrode assembly 500 with an electrically insulating cover 506 and FIG. 5C a perspective view of the same assembly. It is to be understood that the electrode assembly 500 may, for example, be mounted as in the electrode 202 shown in FIG. 2.

Figure 3:
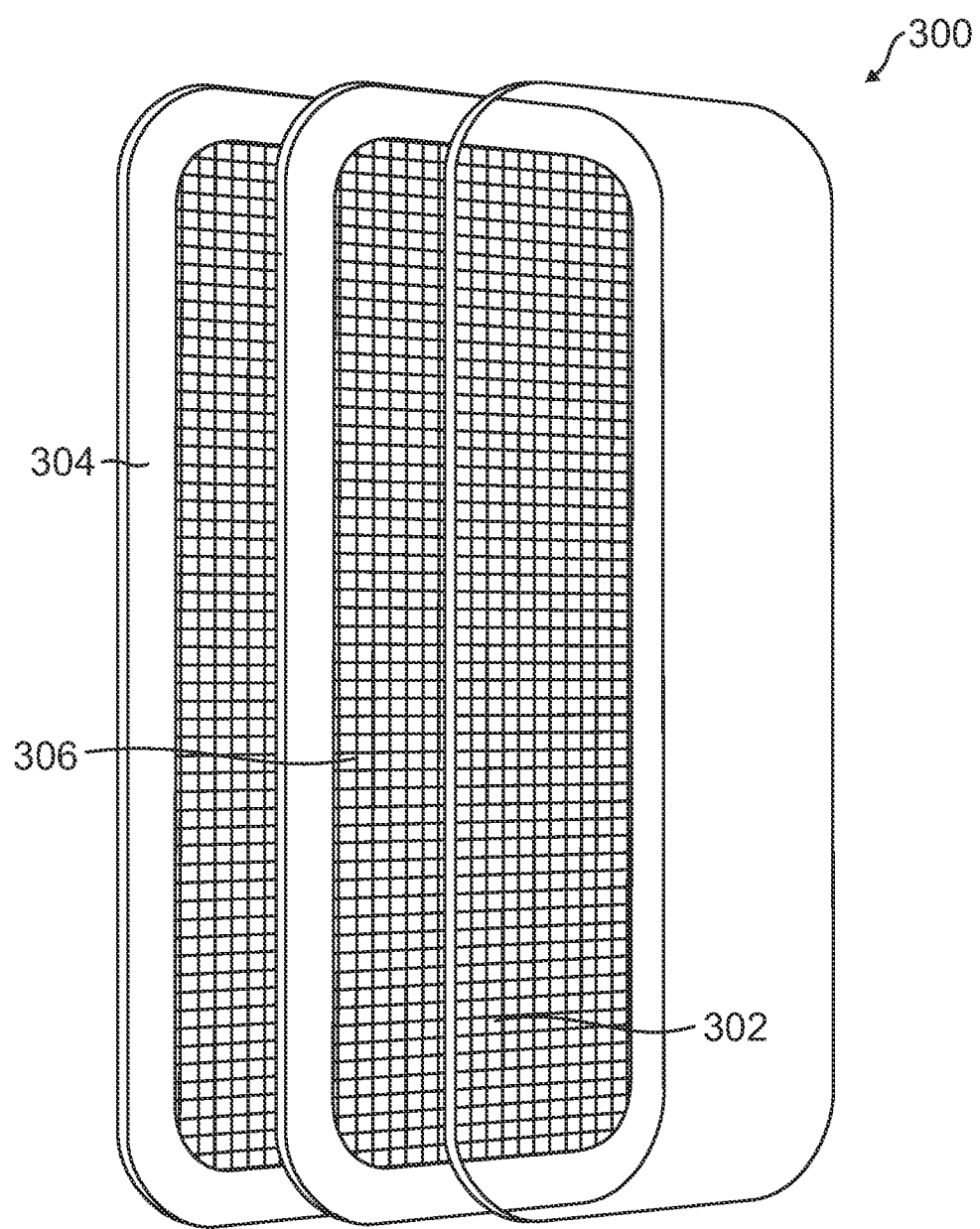
FIG. 3 illustrates a solid gel plate which may be interposed between the skin tissue and the RF electrode(s) side closest to the skin tissue.
Figure 4:
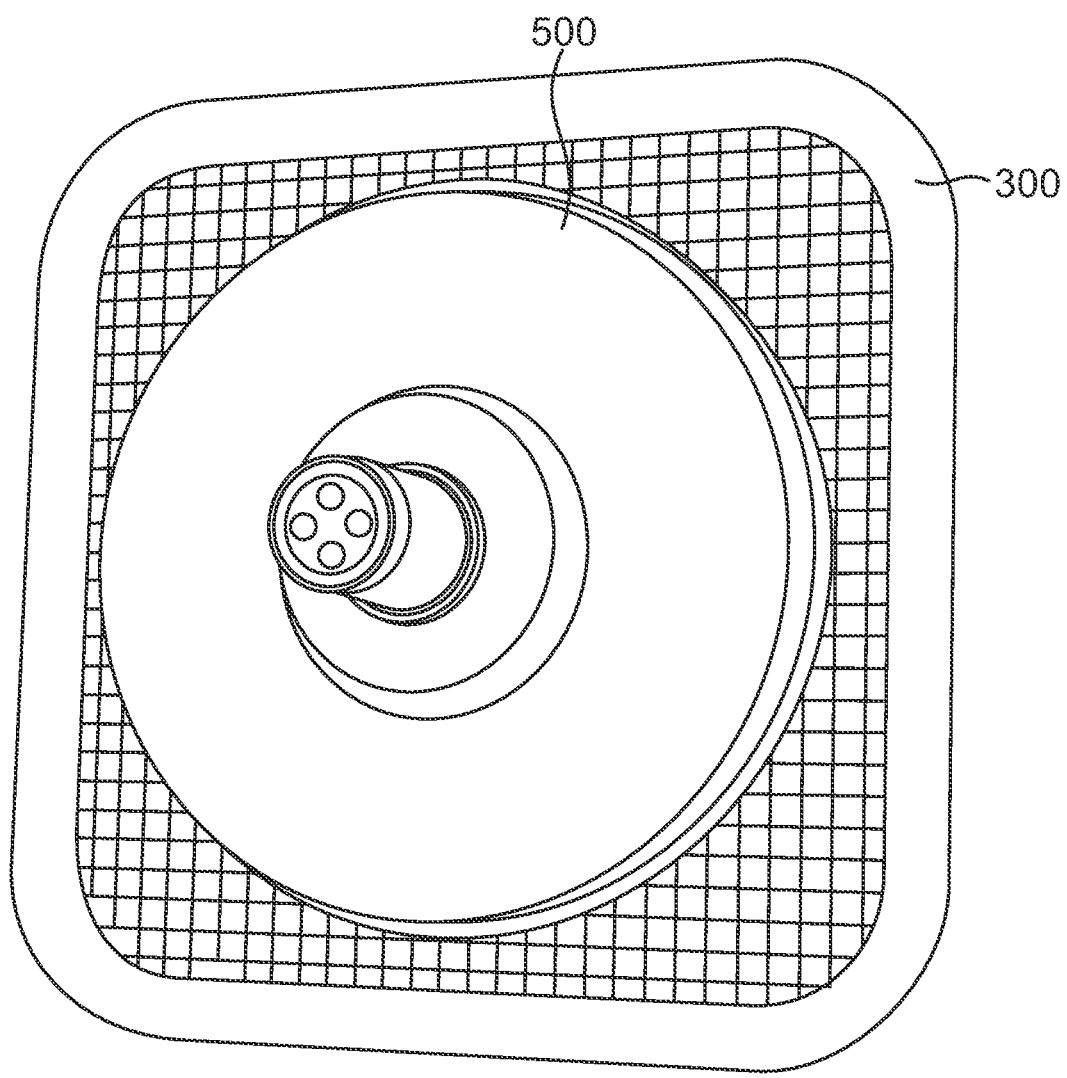
FIG. 4 illustrates experimental results achieved with the device and treatment parameters available in the present invention.

Turning now to FIG. 4, this figure shows a RF electrode assembly like that shown as 500 in FIG. 5 mounted on a gel pad assembly like the gel pad assembly 300 from FIG. 3. The patient's skin tissue to be treated by the present invention is located on the non-visible side of the gel pad 300. It is to be understood that the shape of the gel pad, the shape of the RF electrode assembly and number of pads and electrodes may be determined by the number of openings in a holder assembly like the holder assembly 102 of FIG. 1.

As can be seen in reference to FIG. 1A, it appears that the shape of the electrodes is generally rectangular. However, this is not the only configuration which is workable and desirable. For example, circular electrodes provide a uniform dispersion of radiofrequency energy from the electrode due to their shape. Rectangular and other polygonal shaped electrodes have the disadvantage that at the hard corners, there can be discontinuities in the generation of radiofrequency energy resulting in different heating patterns generated when applied to the skin tissue.

In the electrodes 104 shown in FIG. 1A, while shown as being rectangular in shape by way of example, it is noted that the edges all corners of the rectangular shaped electrodes are rounded so that the differential in radiofrequency energy generation and heating are minimized while still providing electrodes that are large enough to be able to treat large areas of the skin tissue. Other shapes, such as squares or circular, may also be implemented.

While Peltier cooling has been discussed previously, it may be desirable to ensure that the cooling that takes place should be limited to areas around the electrodes, in the vicinity of, but not under, the one or more electrodes for a number of reasons. As shown in FIG. 1A, for example, the central positioning of the Peltier cooler 108 will cause the holder 102 to emanate cooling of the areas of the holder 102 surrounding the RF electrodes 104*a-f*, such that the skin temperature under the holder 102 is more or less around the normal body constant temperature of 28 degrees C., for example.

Thus, with the arrangement of cooling Peltier cells in the present invention, the exact temperature of the skin under the RF electrodes is known, and, as such, the system parameters can be manipulated to deliver the desired amount of heat into the depth skin tissue, during the entire treatment.

Many known RF systems cool the electrode(s) themselves, for example with the circulation of coolant, and the electrode(s) in turn cool down the skin. This is done to avoid pain or discomfort to the patient when reaching temperatures above 42° C.

By maintaining the temperature of a large area of the skin around the electrodes at constant and physiological values (e.g. T=28° C.), through the planar holder 102 of the present invention, even if high temperatures (45° C.) are reached under the electrodes, the patient does not experience an unbearable discomfort or pain, because the microcirculation of the blood drains a portion of excess heat in the area below the electrode. But below the epidermis and at the fat level, the temperature increases steadily until adipose (fat) cells is destroyed.

In addition, the surface of the electrode side which are nearest to the skin tissue may be coated with a thin layer of biocompatible classic material such as PTSD or Rilsan© (medical grade), or be coated with a ceramic material, which is electrically insulated to prevent non-insulated metal electrode causing electrostatic charges of plasma discharges, which in turn may provide discomfort or pain in the form of burns to the patient. Another way to overcome this problem to prevent anywhere occurring on the electrode is to make the electrode of an Aluminum alloy (such as alloy EN AW 6082), with surface treatment with a hard oxide, impregnated with PTFE (medical grade). This may provide long term, extensive use of the electrode without the risk of thinning of the insulation layer away while still guaranteeing biocompatibility.

If the surface or face of the holder 102, shown in FIG. 1B, is placed on the skin tissue, there still may not be perfect contact between holder, its radiofrequency electrodes, and the skin tissue. This may be due to, for example, the stiffness of the material of which the holders made or, more likely, irregularities in the skin tissue surface, such as curved surfaces, indentations and wrinkles in the skin tissue. Should this be the case, the delivery of RF energy may well be nonuniform and may result in uneven heating of the skin tissue. Thus, the holder 102 of electrodes are not pressed down hard by the operator during mounting or any movement of the holder as this can create micro discharges or uneven delivery of energy across the skin tissue surface. This may occur even when a belt is used to secure the holder 102 to the patient's skin tissue.

To reduce this problem, manufacturers presently may employ a water-based gel of the type used in ultrasound treatments which is spread on the skin areas in which the electrodes will be placed. This solution, however, has limits, because with the movement of the electrode on the surface, the gel spreads and partly may be absorbed in the skin, again creating the energy discontinuity problems discussed above.

To remedy this problem, a preferred solution is the use of a solid conductive RF energy gel plate which is placed on the skin tissue and is designed to even out any discontinuities.

Such gel plates are known in the art but, as understood, have not been used in connection with devices like the present invention. The gel plate may be made in three layers: a layer of adhesive gel that contacts the skin, an intermediate layer consisting of a superconducting intermediate grade carbon film (in the form of a thin film or retina layer), and an outer layer of conductive gel adhesive that may be applied to the surface of the electrode or electrodes facing the skin tissue. FIG. 3 shows such an energy gel plate, showing the layers of adhesive conductive gel 302 and 304 and the layer of superconducting intermediate grade carbon film 306.

The energy gel plate described above provides certain advantages. Thanks to the middle layer having intermediate carbon grade, the radiofrequency energy will be distributed to the skin surface homogeneously, so that even heating of the skin tissue occurs. The gel plate also transmits the RF energy very well to the skin to even deep tissues, reducing the skin impedance and therefore lowering surface heating, thus preventing the RF energy from heating the skin more on the epidermis level.

While the carbon film has been described above, it may be advantageous to instead (or even in addition) utilize one or more layers of graphene. Graphene is a known material but is believed not heretofore been used in combination with the other layers of the hydrogel gel pad components disclosed above, nor in the combination RF and EMS device disclosed in U.S. Provisional Application No. 62/884,099, filed Aug. 7, 2019, incorporated herein by reference. Graphene is a material which is an exceptional thermal and electrical conductor, is flexible as well as biocompatible.

As a result, it will be possible to have a temperature at the epidermis level somewhere in the vicinity of 43 to 45 degrees C. without the patient suffering discomforting burns or pain, as localized heating is eliminated or very much reduced, aided by the cooled planar holder that drains excess heat.

The use of a gel plate also allows warming of the tissue to take place faster and produces even higher value temperature of up to 47/48° C. without harming the skin tissue due to the uniform distribution of energy. Thus, placing of the energy gel plate between the skin tissue and the radiofrequency energy generating device avoids discontinuities in skin tissue causing discontinuities in heating of the skin tissue.

Operation and Control of the RF Energy Device

While heretofore the description has been made generally related to the structure of the device or appliance which is applied to the skin tissue, the present section of this application is directed to the control application criteria pertinent to the treatment regime applied to various patients.

In prior art devices, the predominant method of providing RF treatments has been through a pulsed regime, that is, the RF energy is applied in a discontinuous, pulsed manner. In the present invention however, the RF energy may be applied in a continuous manner.

A programmable controller, which is part of the device or a console of the invention herein that provides the RF energy also has the capability, in a generally autonomous fashion, to choose a single or multiple range of frequencies of RF energy to be applied to the skin tissue. The programmable controller may be in communication with a device to measure impedance of the skin tissue. Impedance thus may be measured, then forwarded to the program controller, which will in turn may adjust the frequency applied to the skin tissue.

Preferably, more than one frequency range of RF energy may be employed with the present invention. Preferably these frequencies may be: 0.475 Mhz, 1.0 Mhz, 2 Mhz, 4 Mhz and 6 Mhz, but these may be varied as suits the particular application of RF energy, the treatment applied, and the condition of the skin tissue. Generally, the program controller will change modify the frequency applied based on the temperature to which the skin tissue is raised, impedance measurements, and type of treatment.

Thus, the above-mentioned console may include not only controls for setting the RF energy, but may also include a computer memory which stores, among other things, settings of frequency ranges and times during which such frequencies are applied, in connection with the specific treatment to be applied. Thus, the console may include a user interface through which an operator can not only custom-design treatment regimes, but also may include preprogrammed treatment regimens that may be selected and then applied to the patient's skin tissue.

As an example, the RF treatment device of the present invention may be placed on a patient's skin. As a first step, the treatment device will measure the impedance of the skin tissue and forward that reading to the operator and to the console's user interface. If desired and if the impedance measurement fits within one or more of the preprogrammed treatment regimes, the operator may then push a button or lever to start treatment. The console will then direct the controller apply RF energy to the skin tissue in a sequence of frequencies within the parameters of the preprogrammed treatment regime. Once commenced, sensors connected with the RF treatment device may measure temperature of the skin tissue and impedance levels while the treatment is being provided. The length of the treatment and the frequency of the RF energy applied may be adjusted according to the measurements above. The program controller may include a feedback mechanism that adjusts the timing of the treatment and the particular frequency of RF energy applied in response to measurements of such parameters as skin temperature and skin tissue impedance.

Further, as described above, the treatment device may include multiple RF electrodes that may be activated or deactivated, individually, sequentially, or even simultaneously, in accordance with the particular treatment regime to be applied. Thus, for example, a first RF electrode or electrodes which is/are positioned over a particular portion of the patient's anatomy and skin tissue may be activated while other electrodes contained in the RF electrode matrix may be deactivated or these RF electrodes may be activated to operate at a frequency or frequencies different from that of the first particular RF electrode(s). This arrangement provides maximum flexibility and control and may be controlled autonomously in response to either or both of the setting of a preprogrammed treatment regime or as a result of feedback from either one or both of the temperature sensor or sensors or impedance measurements of the skin tissue.

Having the ability to generate different frequencies of RF treatment from different RF electrodes provide the advantage of achieving different physiological effects in a single treatment. For example, by selecting particular RF frequencies and particular RF electrodes, the patient may be treated in a way that adipose tissue may be reduced while at the same time wrinkles that may already be present, or which may arise from the shrinkage of adipose tissue may also be treated. For example, if the operator intends to perform a skin rejuvenation treatment, the controller, based on the input from the operator on the user interface and based on the impedance level detected, chooses and implements the most suitable frequency according to the treatment desired, which could be a frequency of, for example, 6 MHz, while an adjacent electrode is activated to carryout skin tightening treatment, in which case a controller may choose, for example, a frequency of 4 MHz.

A further advantage of providing different frequencies of treatment is that by doing so and by varying such frequencies, the ability of the human body to react to the heat caused by the RF energy through sweating, pain and or discomfort may be reduced. In changing the frequency of treatment and applying such a continuous manner, heat, which is induced by the RF treatment, spreads progressively and evenly at a similar speed through the various layers of skin tissue so there is only a gradual increase in temperature over the entire thickness of the skin tissue treated, which is not occur when devices operated at a single frequency.

As a consequence, the mechanisms of defense to deal with induced heat within the human body are slower to react, thus allowing a gradual increase in a temperature and even reaching temperature levels important for effective treatment in a way that there is no pain or discomfort due to high localized excess heating. Thus, by operating changing frequencies, the heat generated by the action of the RF treatment spreads more evenly and at a faster pace, while the temperature of the skin tissue rises gradually through the treatment area at different depths of treatment into the skin tissue.

Further, the change in frequency of the treatment regimen of RF application changes the depth into the skin tissue of areas of treatment. Thus, different depths in the skin tissue can be treated by manipulating the frequencies applied. In addition, with the matrix of RF electrodes as seen in FIGS. 1A through 1C, it can be seen that, for example, electrodes 104e and 104d are closer in distance apart than, for example, electrodes 104a and 104d. Thus, activating such pairs of electrodes, in combination with varying the frequencies of application of the RF energy allows the operator to select different depths of treatment into the skin tissue.

As another example, if an operator wants to act both on cellulite and to reduce adipose tissue in a single treatment, a preprogrammed treatment regime may choose a frequency of 1 MHz to treat cellulite while another frequency that best reduces the number of fat cells may be 0.475 Mhz, either by different selected RF electrodes or the same electrodes with different applied frequency changes. It is important, since the physiology of the skin tissue differs somewhat from patient to patient, to know where the desired level skin tissue is located so as to provide the most efficacious treatment regime. This information may be provided through impedance measurements both before treatment begins and during treatment, and such measurements are then fed to the controller in the console which then, in turn, adjusts the particular frequency to be applied and the time during which the frequency is applied to the skin tissue.

Thus, the present invention provides the following advantages over previously known devices and treatment regimes. First, the present invention enables the operator to carry out treatments in a more or less autonomous manner, directed to a particular type of treatment applied to a particular portion of the human skin tissue, based both on impedance measurements as well as skin tissue measurements. Second, the present invention provides the ability to treat multiple areas with a plurality of electrodes, again without operator intervention since it is the controller that measures impedance and skin temperature and adjusts and selects a specific electrode or specific electrodes at selected frequencies. Third, the present invention facilitates the ability to provide treatment at different depths of the skin tissue so that different physiological issues may be treated during the same treatment time that the patient is subjected to at the operator's facility. Fourth, the present invention permits the power applied to the RF electrodes to be controlled automatically by the controller on the basis of the impedance measured, a set target temperature and the particular treatment regime selected. Fifth, by continuously reading impedance and temperature levels, in the event that the temperature level in the skin tissue rises above safe levels, such information may be transmitted to the controller which then either adjusts the treatment regime to safe levels or aborts the treatment altogether.

While the above discussion has been concentrated on a matrix of RF electrodes formed in a more or less planar structure, it is envisioned that the present invention also may apply to different shaped RF electrode holders, including even a small diameter, oval or circular-shaped device which may be employed within a vaginal handpiece. In this embodiment, the use of different RF electrodes to provide different frequencies allows the operator to provide multiple treatment effects during the same treatment, such as, reducing skin laxity as well as activation of the microcirculation of pelvic muscle tissues and even including reducing urinary incontinence.

A Second Embodiment: Transdermal Delivery Methods

Transdermal delivery is a technique that allows active substances to be conveyed into the tissues, in a completely painless and non-invasive manner. The molecules to be conveyed into the tissue, generally microparticles or nanoparticles, can be phytocomplexes, cosmetics and pharmacology according to the therapeutic need.

The basic idea in transdermal delivery is to penetrate the skin barrier so as to be able to transport active ingredients and substances directly into the necessary areas, below the epidermal layer. Use of this technique obviates the need to use needles or syringes for the administration of the substances, nor does it involve the use of acids.

Transdermal delivery makes it possible to convey a greater quantity of cosmetic or medicinal molecules in a completely painless and non-invasive way, which accumulate and spread little by little over time, guaranteeing a prolonged action over time and above all provide greater therapeutic efficacy.

The use of topical medical or cosmetic substances, associated with transdermal delivery, makes possible a very low interaction with the blood circulation, reducing any gastrointestinal toxicity of the molecules conveyed.

This method is effective, has a very high tolerability index and is easy to use for the operator.

With transdermal delivery, the following can be effectively treated: cutaneous hypotonia; wrinkles; water retention and cellulite; stretch marks; localized fat deposits; skin spots; acne scars; toning (not only for the neckline or the arms, but also the buttocks and breast); alopecia; attenuation of neuralgic or muscular pains or real pathologies, conveying in this case ad hoc pharmacological preparations. The most common of these, for example, are: cervical-back pain, tendon calcifications; acute inflammation; muscle contractures; and cicatricial fibrosis.

On a technical level, transdermal treatment has numerous advantages: it is defined as selective, as it is effective locally on the treated areas and does not affect healthy areas; lower quantities of substances can be used thanks to the high percentage of product conveyance; it does not tend to overload the skin and body metabolism; the molecules during vehiculation remain intact and are therefore more effective than those used with invasive methods; and, the results have a natural effect and in most cases are visible from the first treatment sessions.

To carry out transdermal delivery there are various devices such as iontophoresis, devices that emit microcurrents, and recently also by using radiofrequency (RF).

Their use, with a different mechanism depending on the technology, is aimed at overcoming the epidermal barrier by "opening" the "intercellular gates", and thus penetrating in depth with the substances chosen and applied by the doctor or other operator.

Thanks to the high percentage of product conveyance through transdermal delivery, it does not tend to overload the skin and body metabolism. The molecules during vehiculation remain intact and are therefore proven to be more effective than those used with invasive methods. The results have a natural effect and in most cases are visible from as early as the first treatment sessions.

Further, lower quantities of the treatment substances can be used thanks to the high percentage of product conveyance. The skin and body metabolism do not tend to become overloaded. The molecules during vehicular remain intact and therefore more effective than those used with more invasive methods.

Radiofrequency (RF) energy may provide a modern transdermal delivery method and system, but previous RF implementations and technologies have a number of different limitations. First, they are dependent on the participation and activity of the operator, i.e. the operator must continuously move a handpiece with the electrode applied, capacitive or resistive, regardless of the area to be treated. The speed of movement and the pressure is subjective; therefore, the distribution of the active principles cannot necessarily be uniform throughout the area. In addition, a conductive RF cream, often lacking in active ingredients useful both in the aesthetic and therapeutic fields, must necessarily be used. With the massaging movement by the handpiece operator with the electrode and with the increase in heat, the cream may be quickly absorbed and therefore the operator must take several breaks to supplement supplying the cream to the skin surface. Further, typically after the treatment it is necessary to clean the treatment area from the non-absorbed cream to prevent the patient from staining the patient's clothing. Also, only one frequency is typically employed and therefore this results in limited treatment action, since the level of depth of action depends above all on the frequency of the electrode employed.

RF technology often does not control temperature and impedance. The use of conductive substances varies skin impedance depending on the amount present which in some areas will be absorbed while in others not. This variety of impedance in the area to be treated affects the temperature level and the effectiveness of the treatment.

Thus, one purpose of the present apparatus and method is to modify the first-described device and to enable it able to carry out transdermal delivery in an effective way. It is to this subject matter that the present embodiment is directed.

As previously described above, a gel pad is shown in FIGS. 3 and 4 with reference numeral 300 and described further therein.

The present invention includes and adds to the device shown in FIGS. 1A-1C, as well as FIG. 2 and FIGS. 5A-5C, a particular pad which is comprised of an adhesive hydrogel that is biocompatible and conductive to RF energy.

The hydrogel pad may be applied to the area to be treated and the applicator that supplies the RF energy (such as that shown in FIGS. 1A to 1C) A number of differently sized and shaped applicators can be made and then applied so as to cover large or odd-shaped areas on the skin surface, and then activated without the operator having to be engaged during treatment.

As a matter of background, a hydrogel is a colloid formed by polymeric chains of molecules dispersed in water, whose content of the aqueous medium can exceed 99%. From a strictly technical point of view, a hydrogel can be defined as "a three-dimensional, hydrophilic polymer network capable of absorbing large quantities of water or biological fluids".

Different natural compounds can form hydrogels, such as in the case of agar and various polysaccharide molecules, but also artificial compounds such as silicones and polyacrylamide. The presence of numerous hydrophilic groups within the dispersed molecule is fundamental. Given the nature and composition of the hydrogels, these are commonly referred to as hydrocolloids.

Among the different possibilities, hydrogels, thanks to their biocompatibility, are reported, for example, for use as a support for the growth of cells in tissue engineering, in breast implants and in pharmaceutical preparations for the treatment of burns and wounds, thanks to its ability to gradually release the active ingredients it may contain.

Hydrogel therefore represents an excellent support for being associated with both cosmetic and pharmacological or phytocomplex active ingredients.

The gel pad described above and shown in FIGS. 3 and 4 may be made with hydrogels and constructed in a suitable way to deliver RF energy in a uniform way. For some time, it has been possible to realize them with the insertion of these active principles, normally in a nano molecule format, but also with classic dimensions.

The specific hydrogel of the present invention may have an acid-base characteristic, which allows the controlled release of a drug or cosmetic active ingredient. There are natural hydrogels such as the Agar or artificial ones such as pNIPAAM (poly-N-isopropylacrylamide), PVA (polyvinyl alcohol) or PVP (polyvinylpyrrolidone).

To carry out its therapeutic effect desired, an active ingredient must be available in a certain dose for a given time in a specific place. Therefore, controlled release systems capable of satisfying these requirements must be appropriately designed so that the active principle can be released with the desired kinetics, in response to some external stimuli (sensitive systems), and/or in certain environments (systems for targeted administration).

Hydrogel-based release systems are excellent candidates when there is a need for controlled release, as is currently widely used in various fields (pharmaceutical, agri-food, etc.).

The hydrogel used in the gel pads has been suitably modified in the chemical structure to make it "stimuli-responsive", that is, to make its properties change in response to external stimuli, such as temperature variation, for example.

Following an increase in temperature and upon reaching the desired temperature, the controlled and slow release of the active material will be introduced into the hydrogel lattice.

Therefore, types of hydrogels will vary depending on the active ingredient inserted and the aesthetic or therapeutic purpose.

By way of non-limiting example, if it is desired to treat periocular wrinkles, hyaluronic acid can be used in the hydrogel lattice so that it can be released at 39° C. following the supply of energy by RF.

When it is desired to introduce the active ingredients to a skin tissue depth to help the destruction of fat by the heat brought to 45° C. by RF energy, typical active ingredients useful for this purpose may be selected from caffeine, and phosphatidylcholine, etc. which will be released starting from 40° C. rather than 42° C., depending on the type of body fat, if abdominal rather than present in other parts of the body.

A Third Embodiment: RF Combined with an Ems/Magnetic Source

Another aspect of the present invention is a modification of the device shown in FIGS. 1A-1C through 5C and described above. The modifications are shown in the embodiments of FIGS. 6A through 6H as well as FIGS. 7A and 7B.

The above description of RF energy application discloses the heating of subcutaneous fat to a temperature of 45° C. and its maintenance for a few minutes; this causes the induced destruction of fat cells, in a non-invasive way. At those temperature conditions, the fat cells degenerate and are phagocytosed by apoptosis from healthy cells.

The liquefied fat that escapes from the fat cells partly crystallizes and partly fills the intracellular spaces, from which it is removed more or less slowly from the venous lymphatic system in the days following the treatment.

But, if the patient's venous lymphatic system is not enough efficient, the liquefied fat still present in the intracellular spaces is slowly reabsorbed with the development of new adipose cells, making treatment efficient in only a limited way, according to the physiological conditions of the patient at the time of treatment.

To overcome this limit in the amount of fat and cellulite that can be effectively reduced, at the same time as the action of the RF is delivered by the device, through applicators which are positioned on the specific area of the skin tissue, High Intensity Magnetic Energy impulses may be able to provoke powerful muscle contractions.

High-Intensity Magnetic impulses can create induced currents which, associated with RF-induced heating, can generate powerful muscle contractions known as muscular thermostimulation.

Typically, electro-stimulation is used for muscle contraction. Electrical stimulation is usually obtained by applying a current to the surface of the body, using electrodes in contact with the skin. This current generates an electric field in the underlying tissue, causing the stimulation of nerves and/or muscles when the electric field in nerve/muscle cells is above a certain threshold.

The stimulation generates muscle contractions that increase blood flow in the muscle and consequently increase muscle strength.

The electric field induces muscle contractions in two different ways.

The first method is the stimulation of motor neurons (nerve cells) which then excites the muscle fibers by chemical transmission. A single motor neuron innervates many muscle fibers. One motor neuron and the muscle fibers that the neuron innervates are called "motor unit". All the muscle fibers in a motor unit contract together and develop strength when they are stimulated by the motor neuron. This type of muscle stimulation is "passive" and is generated by electro-stimulation.

The second method is direct stimulation of muscle fibers (muscle cells). Muscle fibers are cylindrical cells of 50-100 um in diameter. Sometimes they extend for the entire length of a muscle. Muscle fibers are grouped into bundles surrounded by connective tissue. The contraction occurs due to changes in the current/electric field applied to individual muscle fibers by the electrodes. This active stimulation happens due to the currents induced by the high-intensity pulsed magnetic field.

Therefore, the electric field and the electrical current induced directly into the muscle is an important factor for the purpose of muscle contraction, rather than the current applied to the skin. Besides, an electric current applied directly to the skin may cause harm and cause burns if it is too intense.

Contractions of the muscle bands induced by impulsive currents generated by high-intensity pulsed magnetic fields, unlike the muscle contractions resulting from classic electro-stimulation on the skin, are powerful and wide, and create a "pump effect" on the venous and lymphatic circulation system effectively removing the liquefied fat still present in the intra-cellular spaces, avoiding fat re-absorption.

In addition, fat heating induced by RF indirectly involves the muscle bands, and this improves the overall capability of the muscles.

It is a known art in physiotherapy that the high intensity magnetic field impulses emitted by the applicators cause currents induced in the covering tissues causing the contraction of the muscles also placed in depth.

The level of muscle contraction and the depth of action of magnetic muscle stimulation depends on the level of intensity, which is normally between 1T and 2T.

But if the muscle is not "ready" to contract the effects of the magnetic pulse on the muscle is reduced.

Athletes who perform competitive sports activities, before starting such activities, perform physical exercises with the aim of "pre-heating" the muscles.

By pre-heating the muscles and keeping them at a constant temperature throughout the treatment by supplying RF, muscle contraction reaches its maximum level.

It has been verified that the ideal temperature at which muscles optimize their viscoelastic characteristics is about 39°/40° Celsius. At this temperature, the speed of muscle contraction increases by 20%, because blood flow increases, activation of sensory receptors improves, tissues viscosity decreases, elasticity of tendons improves nervous conduction speed increases, and enzyme activity changes positively.

In conclusion, the synergy of RF-induced heating and muscle contractions as a result of intense magnetic field-induced electrical currents, produces the following effects:

Radiofrequency-induced heat forces the lipid panel to expel intra-cellular fluid in order to compensate for the thermal action. The liquid leaked from fat cells as a result of the induced heat is then removed quickly from the affected area thanks to the active contraction of the muscles, stimulated by the vibrating platform. Therefore, there is an immediate, verifiable and effective venous-lymphatic drainage, as well as the re-activation of microcirculation that completes the elimination of intracellular fluids in the following days;

More powerful and intense muscle contraction, resulting in increased muscle toning, firming, and strengthening;

Production of testosterone due to muscle contractions. Testosterone is the inhibitor of the formation of fat tissue;

Muscle thermostimulation, produced by the association of muscle contraction with RF-induced heating, creates an intense peripheral vasodilation action which tones the skin and prepares it to absorb the active ingredients contained in cosmetic products.

The devices shown in FIGS. 6A-6H differ from those of FIGS. 1A to 1C in that an EMS (Electro Magnetic Stimulation) coil is included in the pad-like structure/applicator/pad.

Figure 6A:
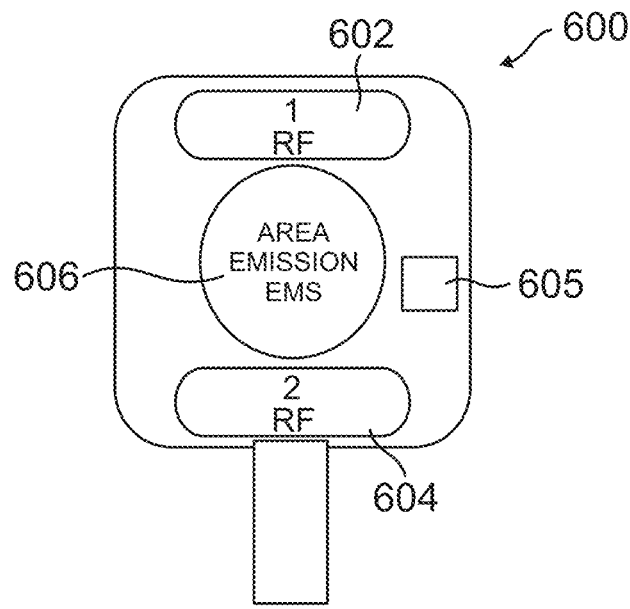
FIGS. 6A-6H illustrate a modification of the embodiments of FIGS. 1A-1C to include a source of electromagnetic energy.

Turning first to FIG. 6A, that figure shows a pad 600 that is shown including a positive RF electrode 602 and a negative RF electrode 604, thus forming a bipolar RF circuit. Further, an EMS coil 606 is positioned centrally on the pad 600.

Figure 6B:
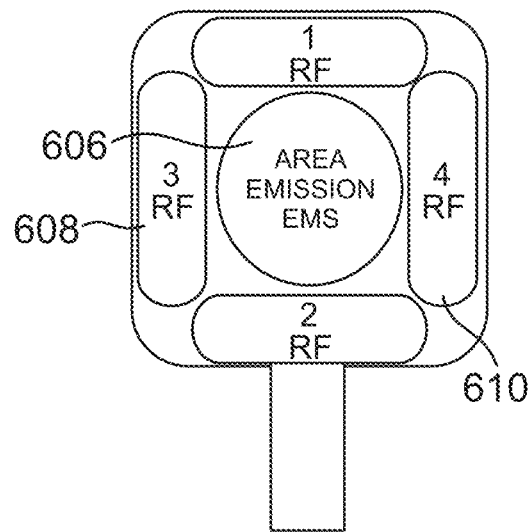
Figure 6C:
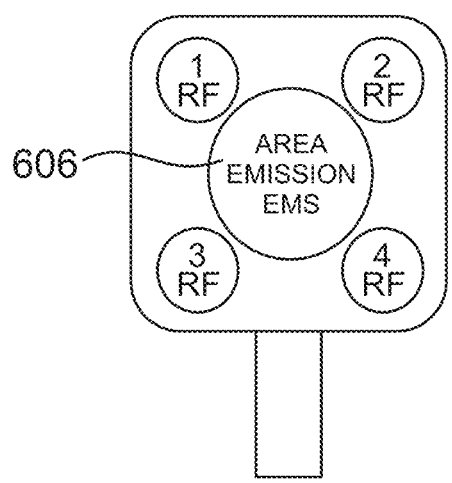
Figure 6D:
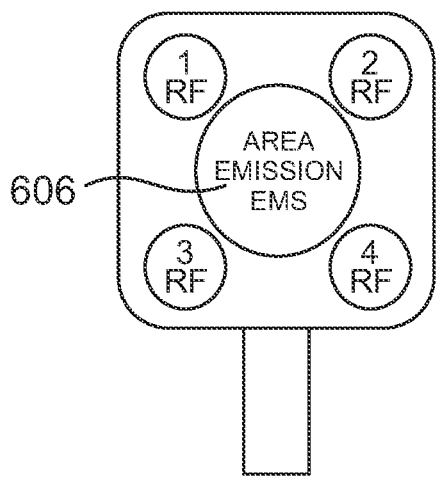
Figure 6E:
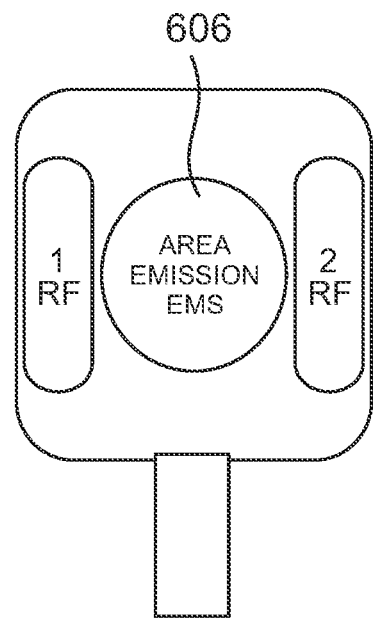
Figure 6F:
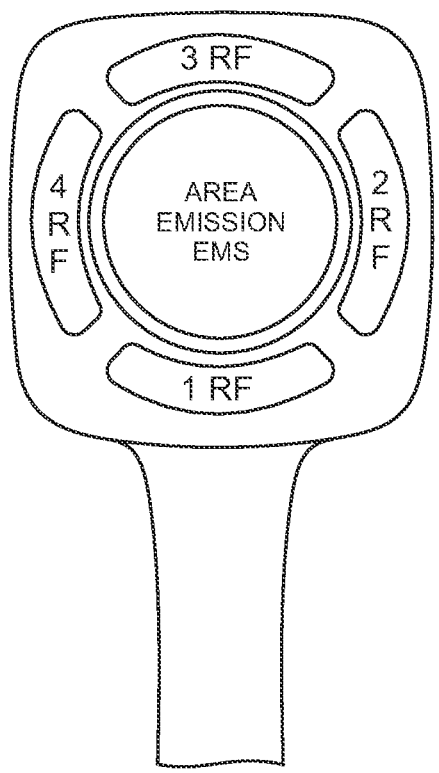
Figure 6G:
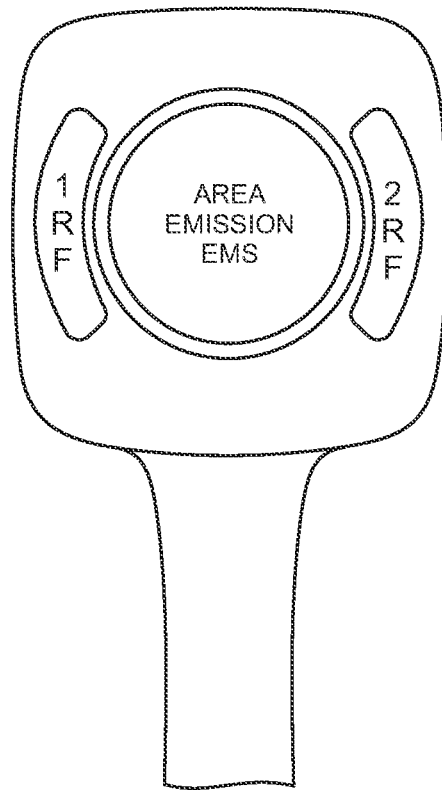
Figure 6H:
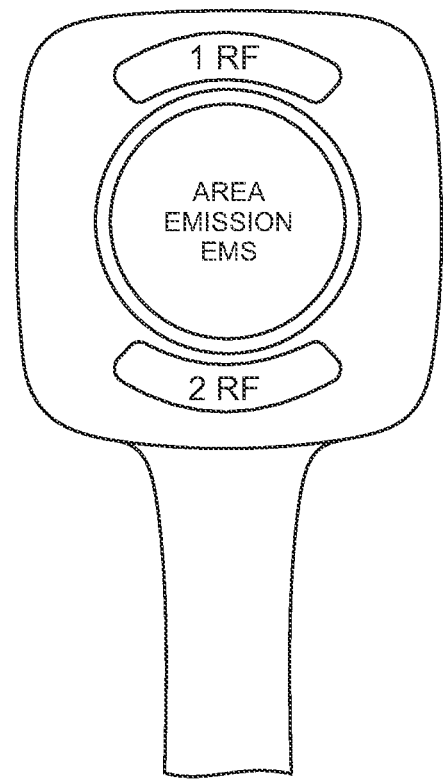

FIG. 6B is similar to FIG. 6A, except with the addition of a further pair of electrodes 608 and 610.

Figure 7A:
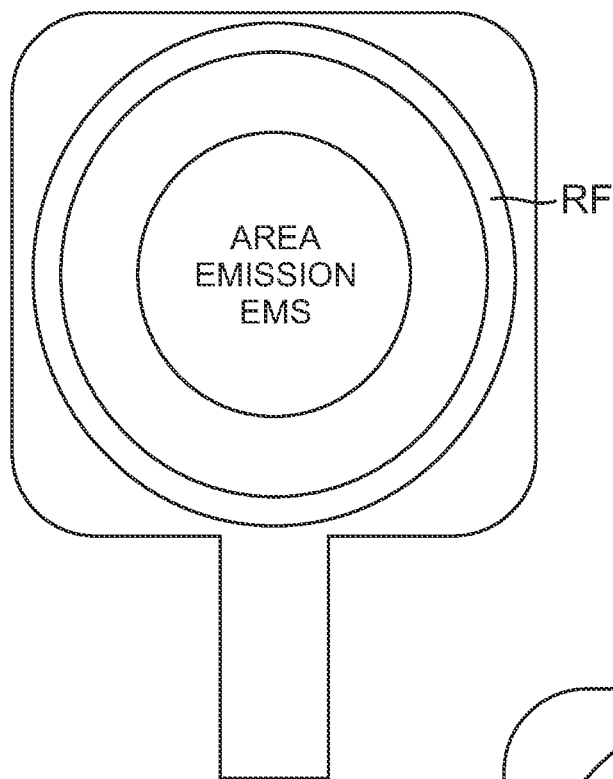
FIGS. 7A and 7B illustrate monopolar and bipolar applicators.
Figure 7B:
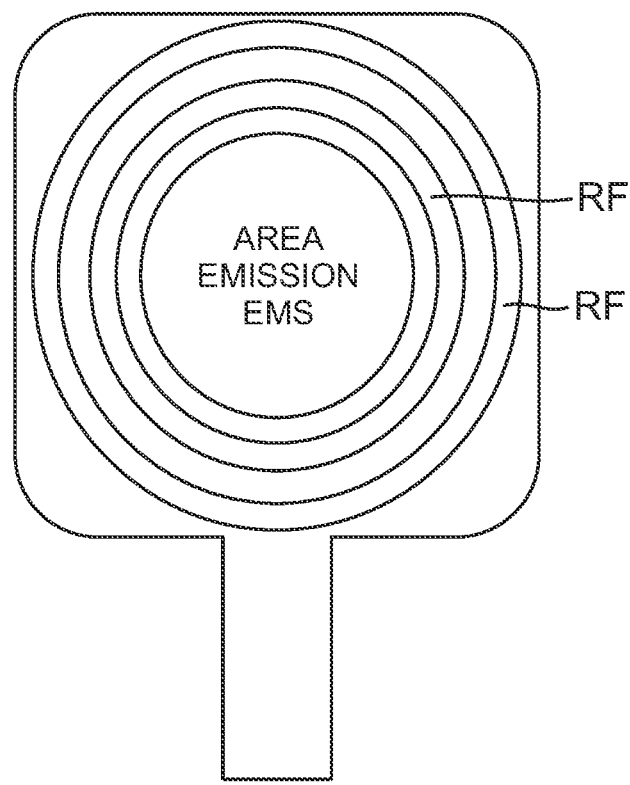
Figure 8A:
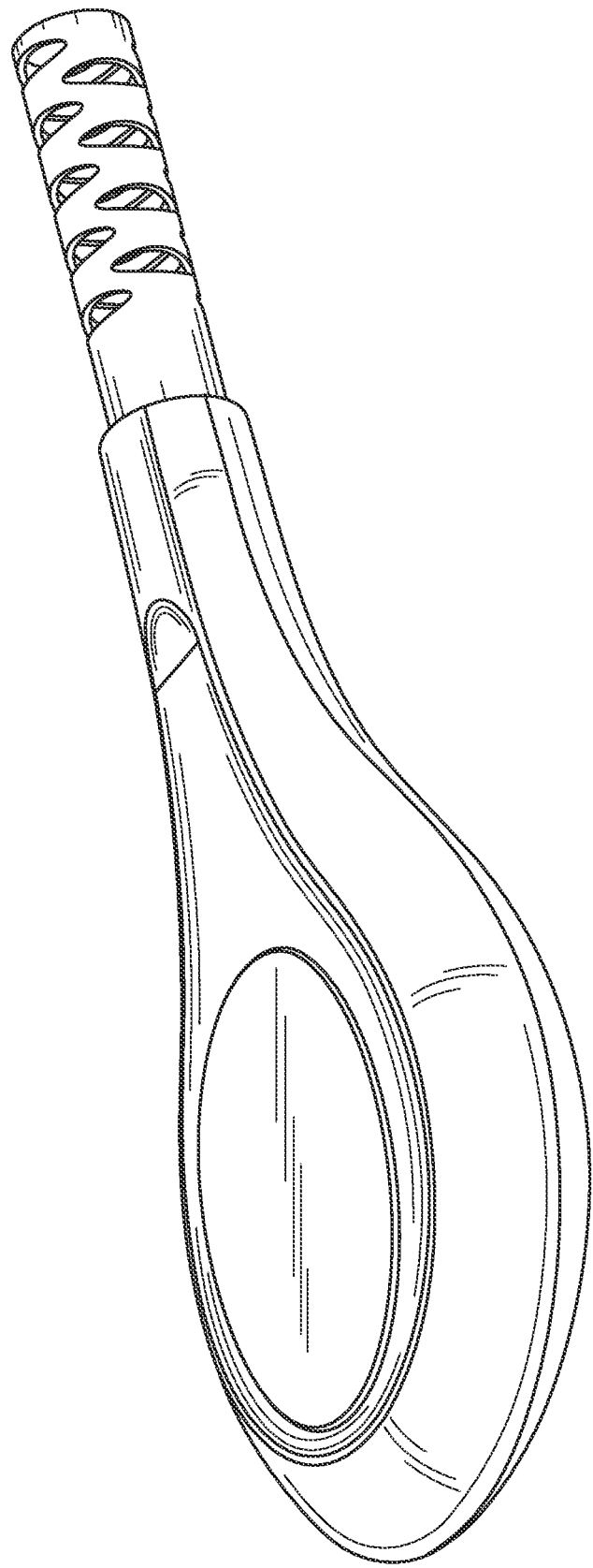
FIGS. 8A through 8H illustrate the structure and design of an energy applicator.
Figure 8B:
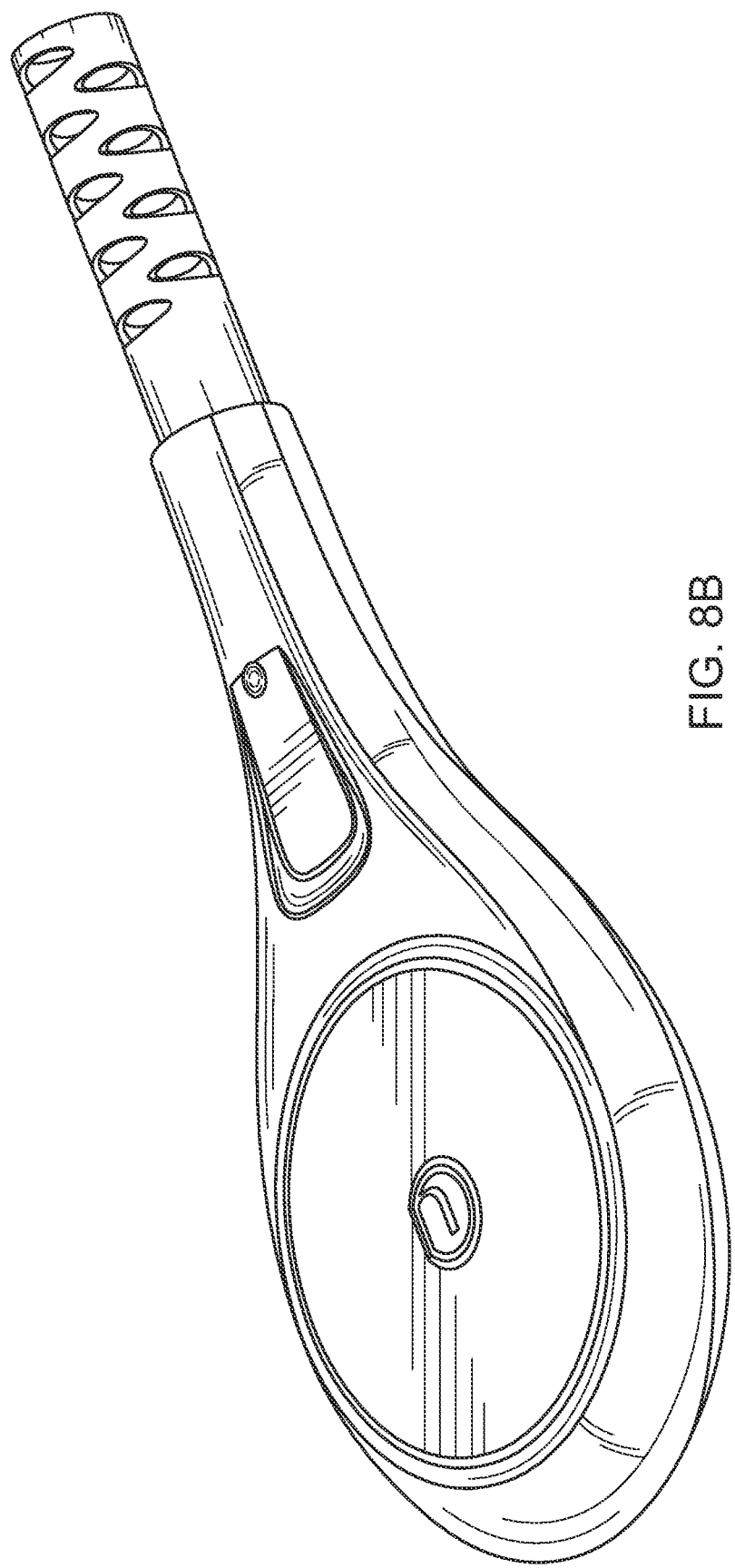
Figure 8C:
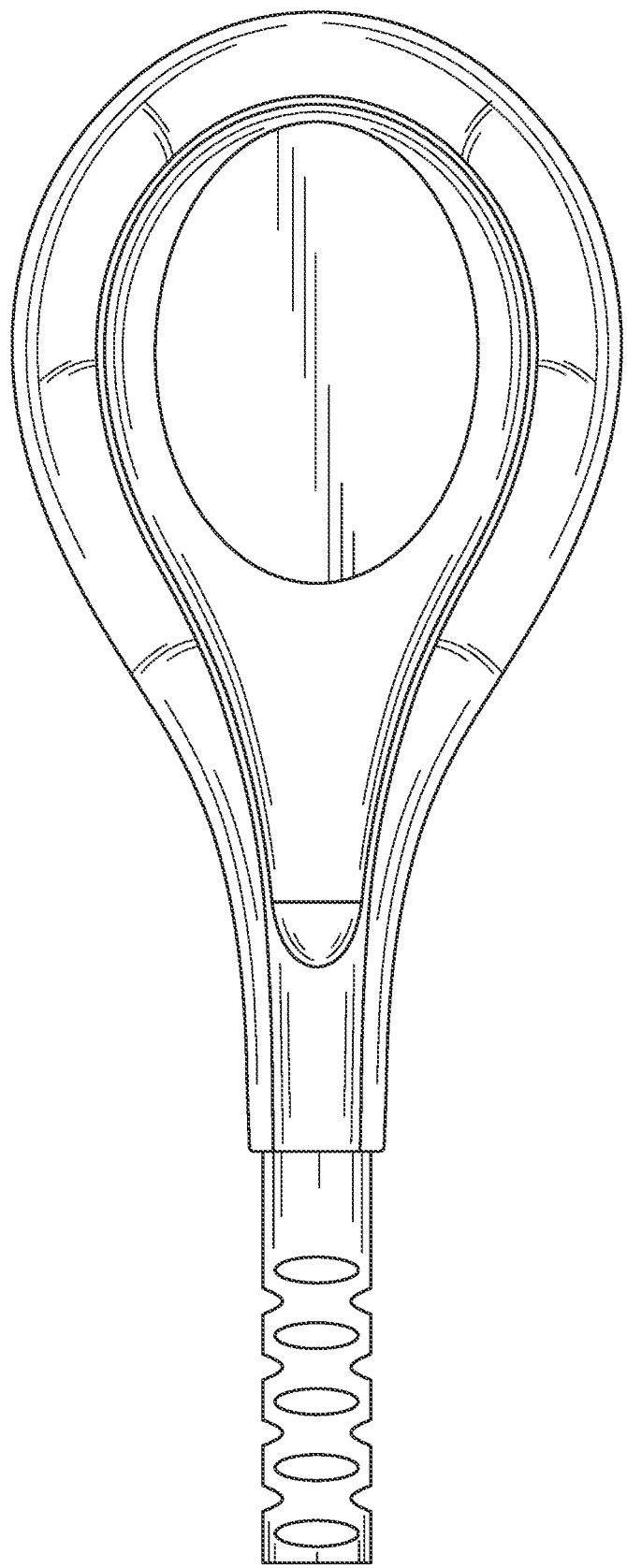
Figure 8D:
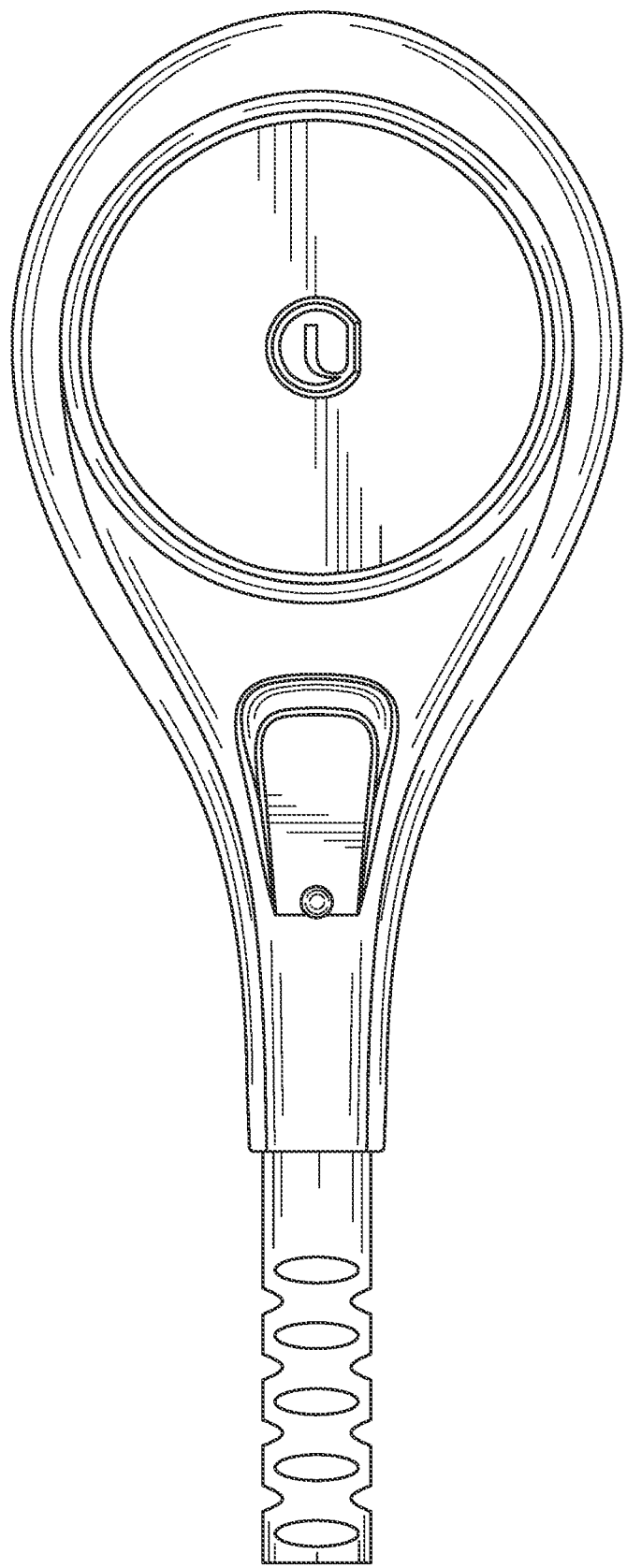
Figure 8E:
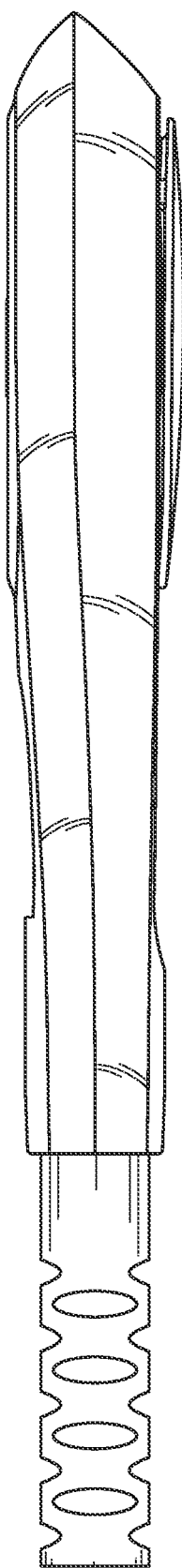
Figure 8F:
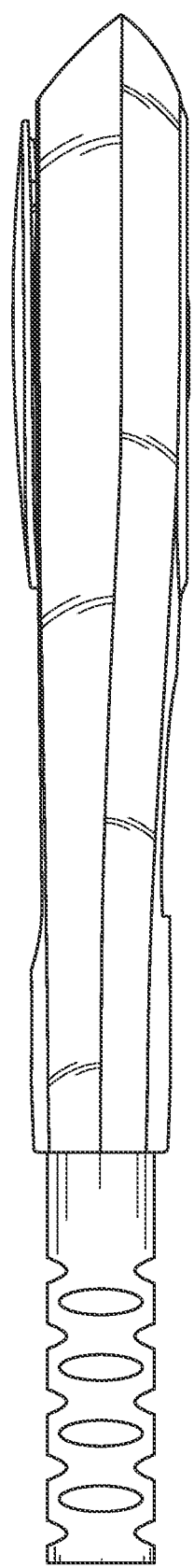
Figure 8G:
Figure 8H:
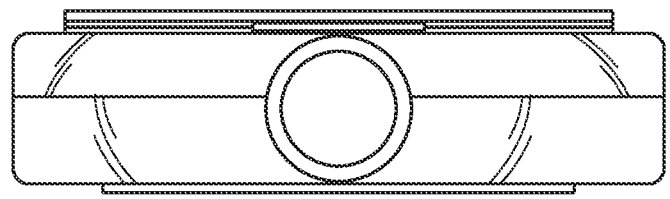

FIGS. 7A and 7B illustrate implementation of the combined RF/EMS in a monopolar setup and bipolar setup, respectively.

FIGS. 8A through 8H illustrate the design of an applicator that may be RF only or RF combined with EMS, or even EMS only. For example, in FIGS. 7A and 7B, the RF electrodes may be eliminated so that the device is EMS only. Further, a suitable console device may contain separate EMS and RF handpieces so that RF and EMS may be applied to the patient either simultaneously or sequentially in any desired order: RF then EMS, EMS then RF, RF and EMS together. In addition, a source of skin cooling may be applied to the patient's skin tissue, this giving three modalities: RF, EMS and cooling. All or only some of these may be applied and they may be applied in any desired sequence or order suing all or only some of RF, EMS and cooling. For example, RF may be applied then cooling, or EMS then cooling.

Figure 9A:
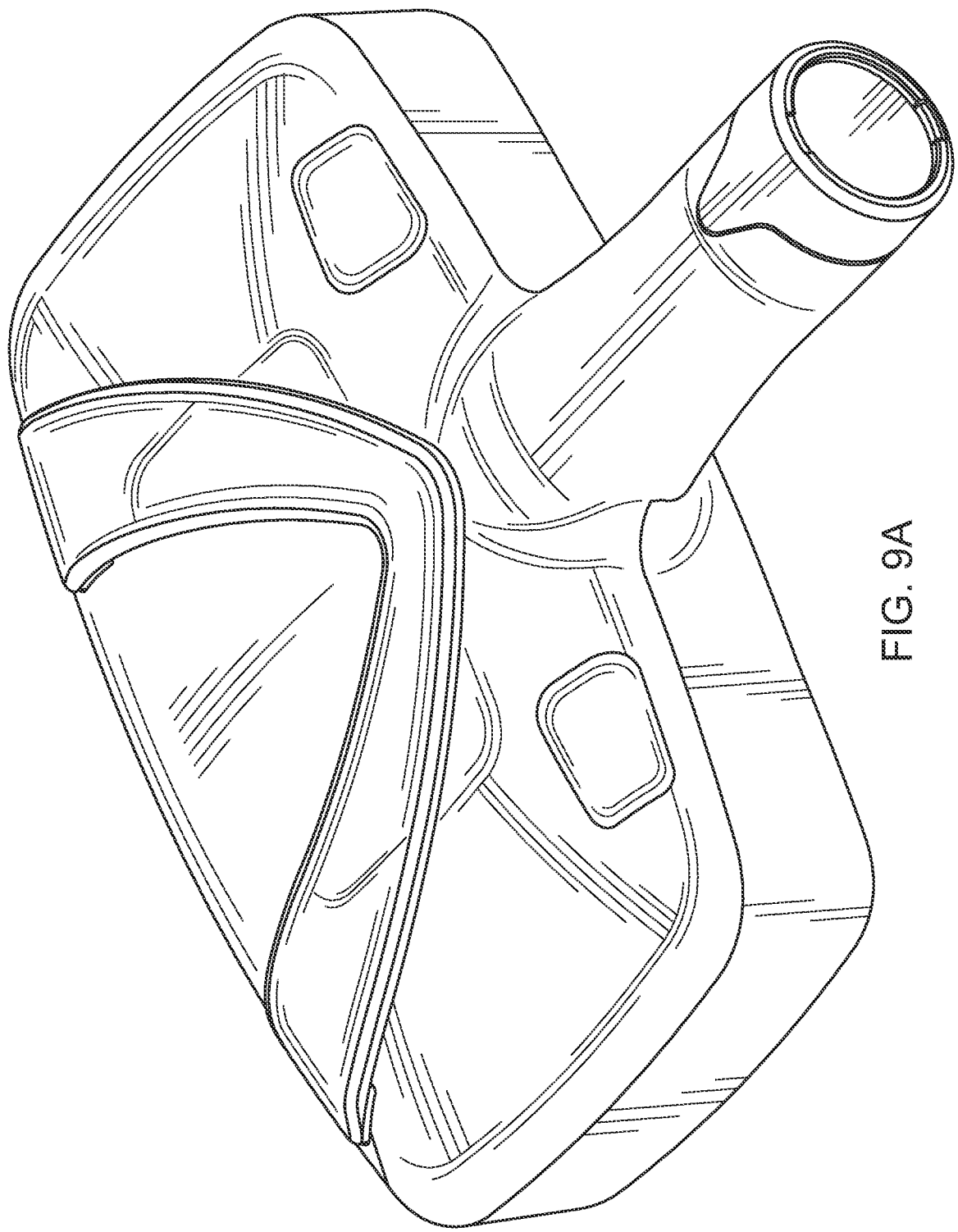
FIGS. 9A through 9H illustrate the structure and design of another energy device.
Figure 9B:
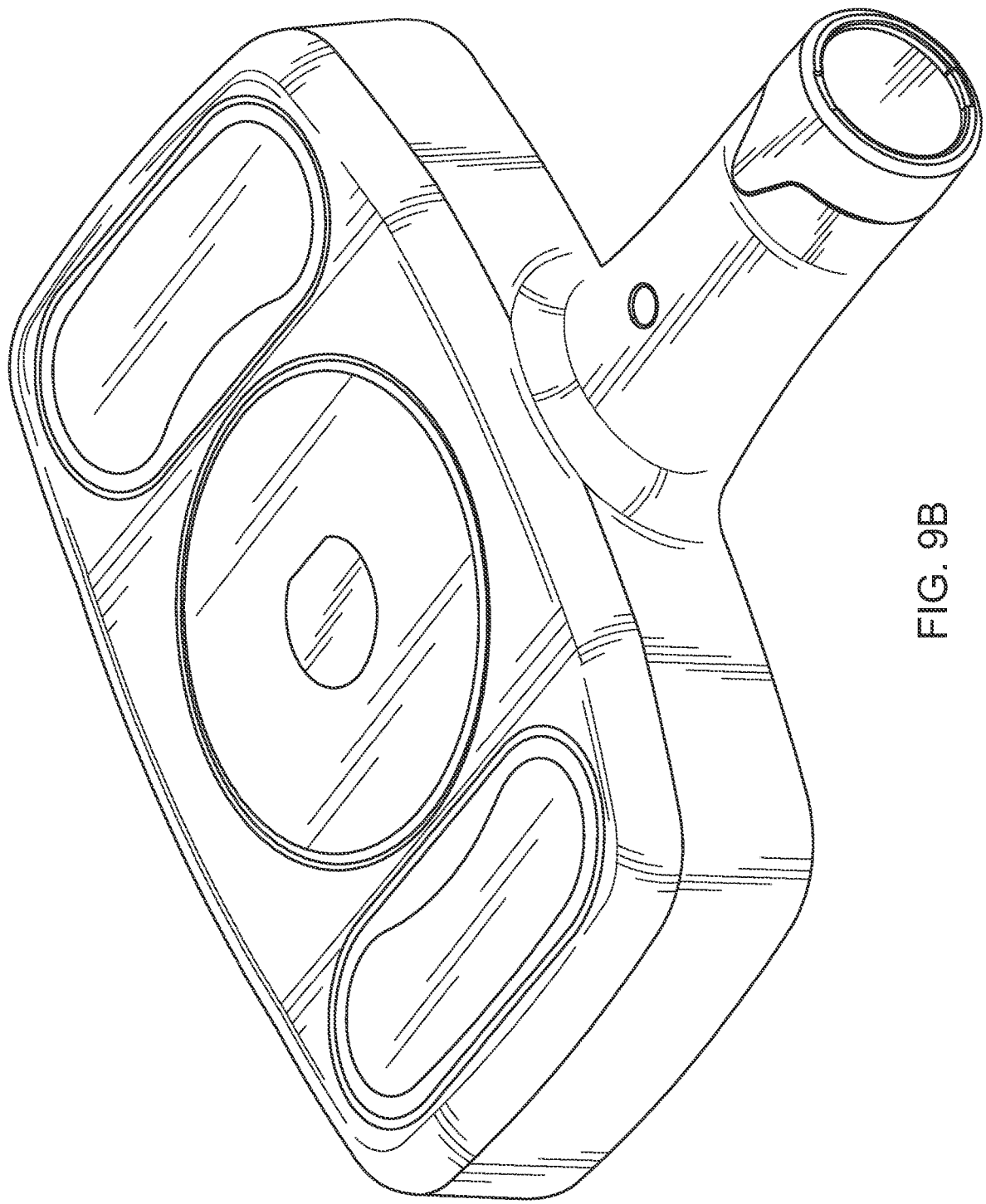
Figure 9C:
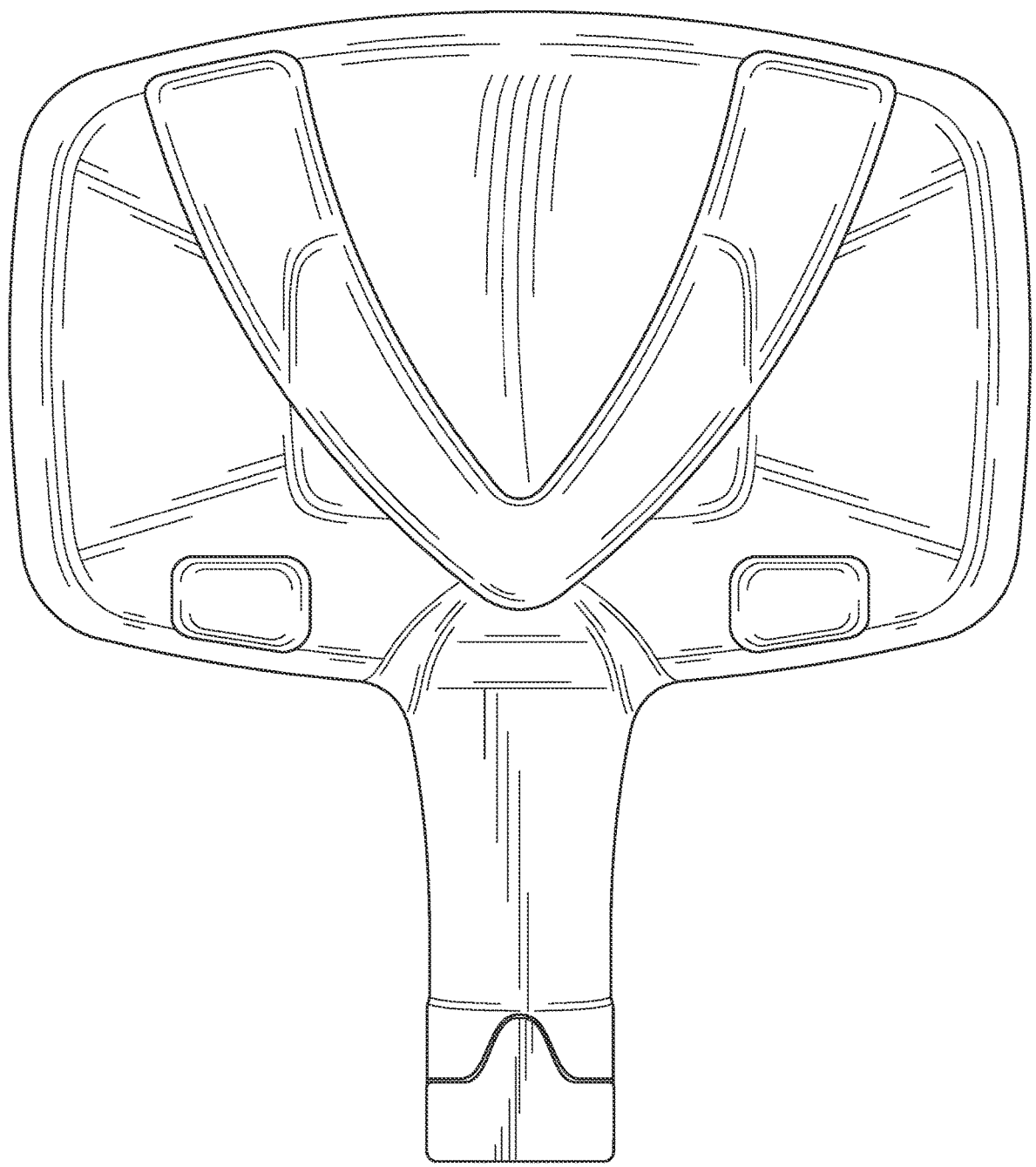
Figure 9D:
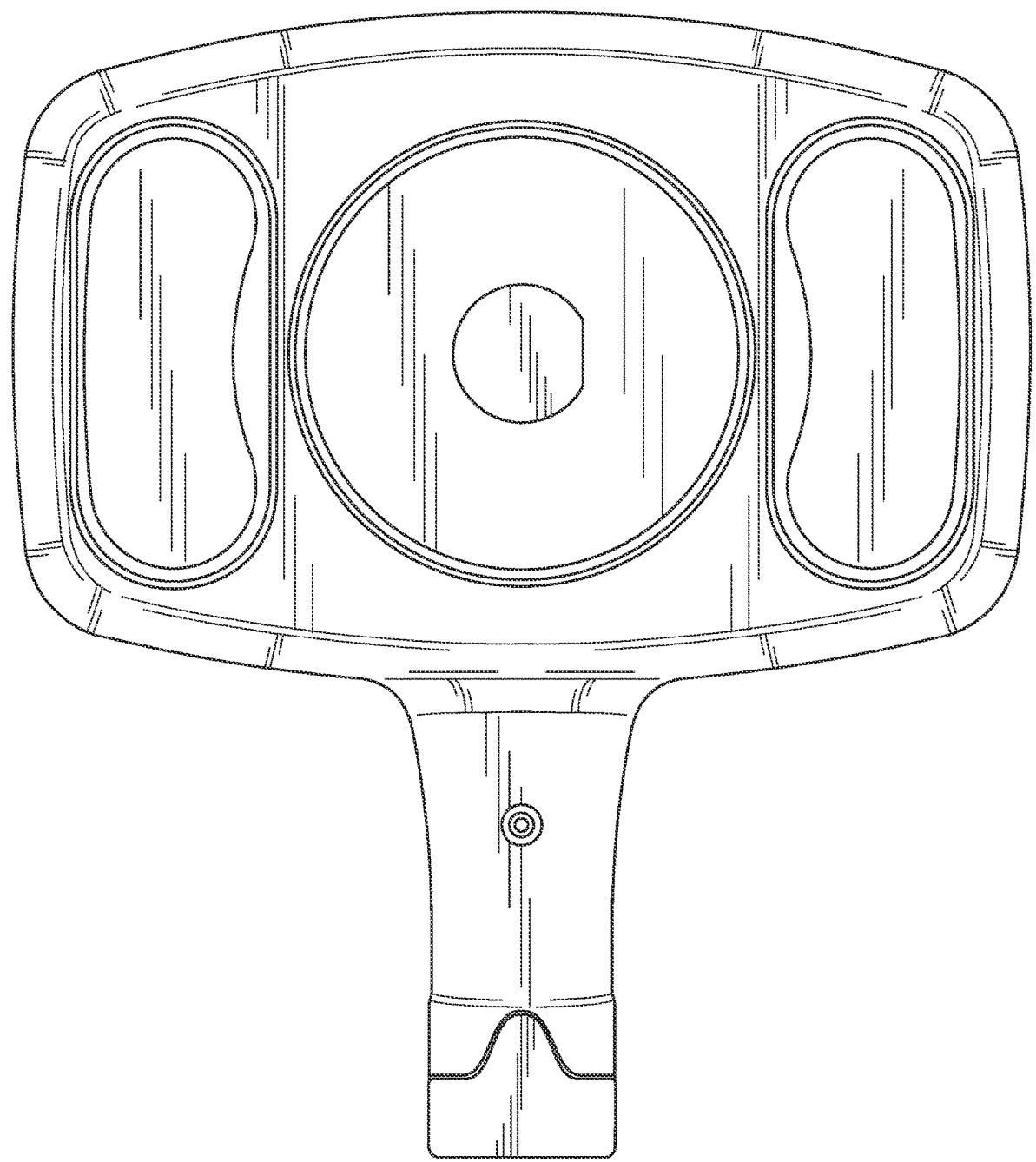
Figure 9E:
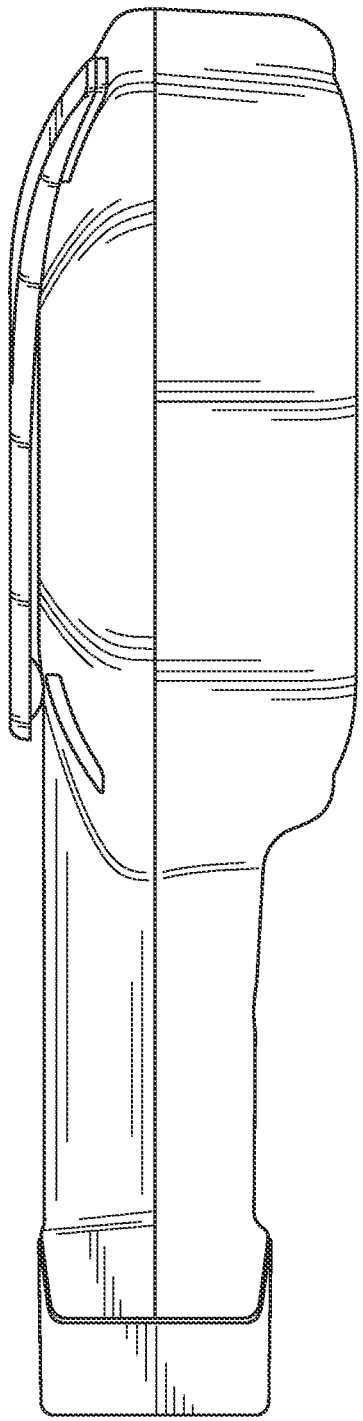
Figure 9F:
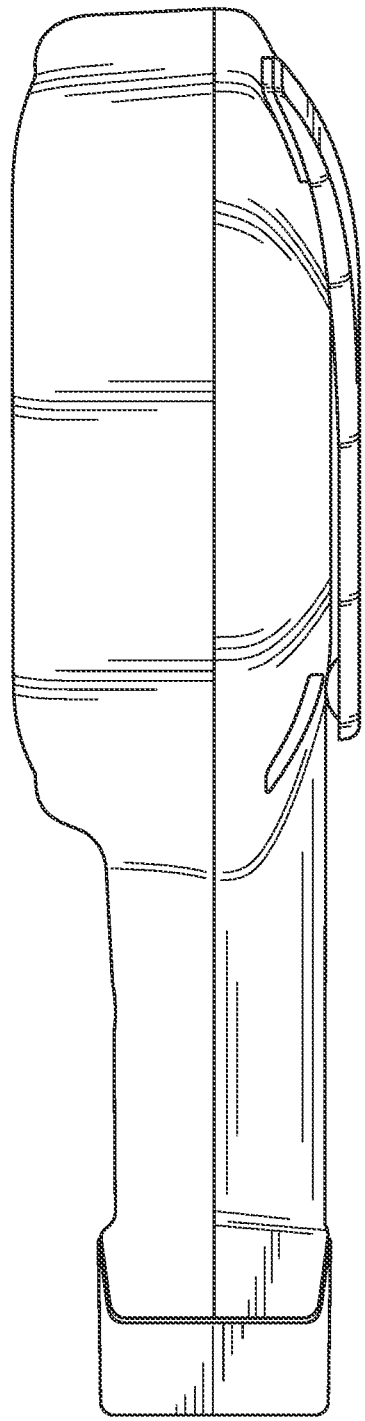
Figure 9G:
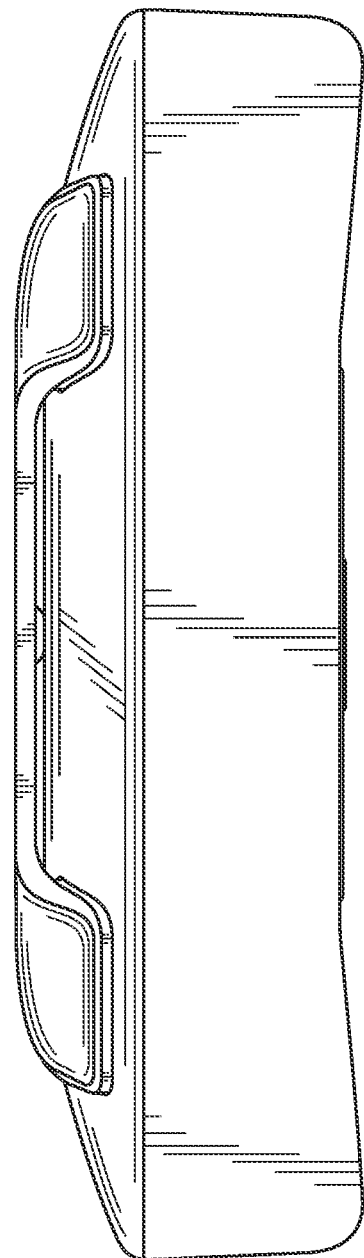
Figure 9H:
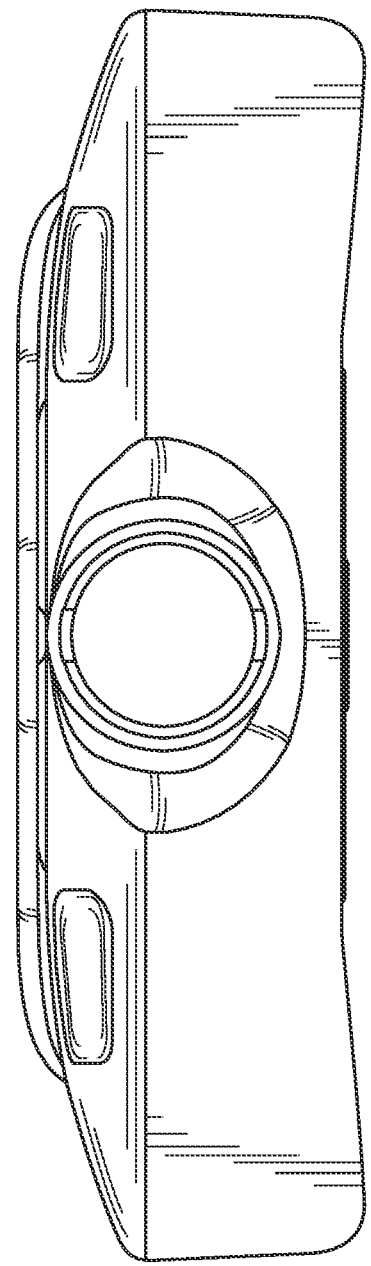
Figure 10:
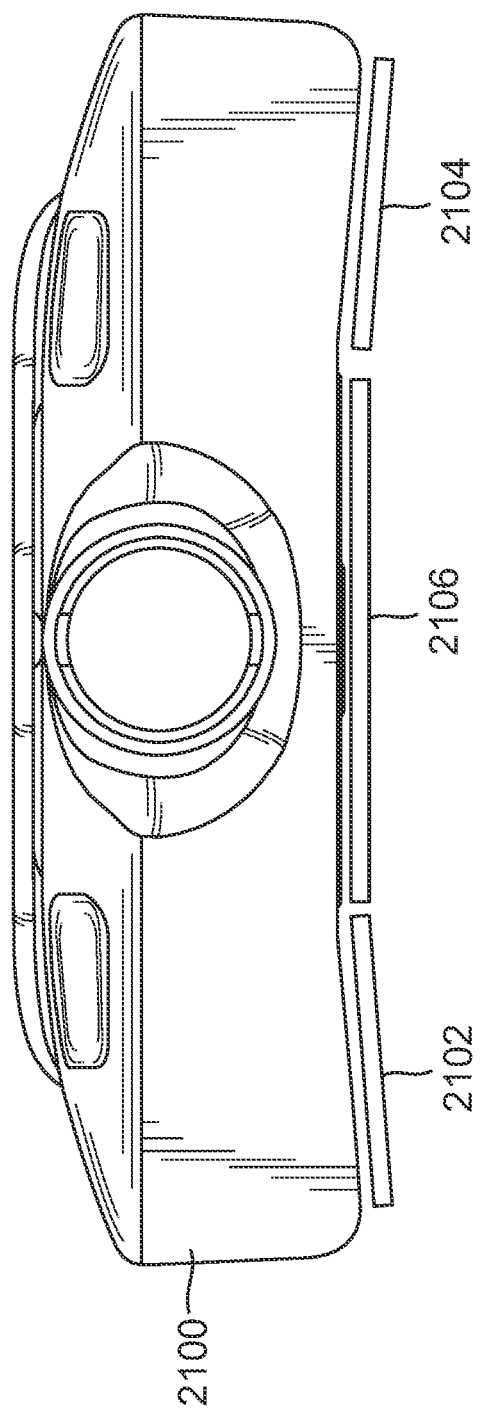
FIG. 10 illustrates a combination applicator having one or more gel pads positioned to interface with the skin tissue of the patient.

Also, the gel pad 300 of FIGS. 3 and 4, which was described in connection with the RF pad and being places between the patient's skin and the RF device may also be effectively used in connection with either a combined RF and EMS device or an EMS-only device, such as that shown in FIG. 8, again being placed between the patient's skin and the EMS handpiece. In fact, in the embodiments shown in FIGS. 8 and 9, the gel pad(s) may be situated under the RF portions or under the EMS portion of the applicator or both. In addition, in the case of the positioning of a gel pad under one of the RF or EMS portions, but not the other portion, the plate or other surface which may contact the skin may be extended to encompass the gel pad portion such that the portion not having the gel pad comes into contact with the skin of the patient. By way of example, FIG. 10, derived from FIG. 9H, shows a side end view of a combined RF and EMS applicator 2100 having three pads 2102, 2104 and 2106. The pads 2102 and 2014 are positioned under the RF portions of the applicator and pad 2106 under the EMS coil(s) portion of the applicator 2100.

Obviously, the number of RF electrodes and even the number of EMS coils may be increased as desired depending on the desired treatment. In the case of multiple RF electrode pairs and EMS coils, they may be wired so as to be selectively activated by a suitable programmable controller.

FIGS. 6C through 6H illustrate various possible modifications of the structure/applicator/pads of FIGS. 6A and 6B.

Further, the sequences of activations may be variably controlled, such as simultaneous or sequential activation of the RF electrodes and the EMS coil(s); they may be operated at a single frequency or multi-frequencies, as described in the above-mentioned patent application.

In addition, again as described above, an adhesive pad between the pad 600 and the skin tissue may be inserted or not inserted, and the belt 106 of FIG. 1A may be provided (or not) to secure the pad 600 to the patient's body.

The device of the present invention operates at frequencies ranging from 300 Khz to 4 MHz and thus at much lower frequencies than in the prior art; thus it acts on deep tissues, and is absorbed for the most part by the fat, reaching preferably the temperature of 45° C., with its maintenance and control by the system, but could also heat up to 50° C., with the added benefit of not causing burns on the skin.

Moreover, the device of the present invention simultaneously emits to emission of RF energy, through a particular applicator or handpiece supported and fixed on the area to be treated. Also, the high intensity pulsed magnetic energy (EMS) is able to generate muscular contractions of considerable intensity. The emission of RF and EMS energy can also take place simultaneously, separately or sequentially with preset periods of action and pauses for the activation of each such energy source.

The high intensity pulsed magnetic (EMS) energy is inputted in the central area, but it is possible to invert the RF energy in the center and on the sides the emitting coils producing an intense variable field of the applicator, and with a magnetic field intensity that can reach 3T. The applicator may have different dimensions to adapt it to the areas to be treated, but preferably square, rectangular or round, example of which are illustrated in FIGS. 6A-6H.

The applicator, one or more applicators per device, but preferably two, may be equipped with an accelerometer 605 capable of detecting the level of oscillation following the setting of the parameters that allow the muscles to contract and release.

For example, the operator may position the applicator on a non-stimulated muscle band and indicate to a suitable controller on a machine that this is the starting zero position. From this point, an operator can then set the usual parameters such as frequency and intensity to check by the accelerometer how much the muscle lifts.

If the operator does not evaluate it satisfactorily, move the applicator and/or modify the parameters to get a better answer.

The applicator has a shape that allows it to house the electrodes from which the RF will be emitted.

The electrode numbers may be more than one and placed all around the vicinity of the area from which the High Intensity Magnetic (EMS) Energy is emitted.

RF emission, therefore, may be capacitive if the electrode surface is electrically isolated, or resistive, if the surface is electrically conductive. Depending on the disposition of the electrodes, the emission can be bipolar or monopolar (with return plate). The electrodes may be circular, or rectangular, oval, etc.

The applicator with RF electrodes will be placed on the area to be treated even without any conductive medium, and adhered to the patient's body with elastic bands or belts or straps, etc.

However, in order to reduce the skin impedance for a better penetration of the RF, between the supporting surface on the skin of the applicator and the skin itself, it may be useful to insert a conductive medium, such as, in a non-limiting example, a RF conductive gel, or gel cream.

Preferably, it may be useful to apply on the surface of the applicator that comes into contact with the skin, a particular double-sided gel pad disclosed in the main portion of this application, of such size to cover the entire surface of the applicator. A pad with hydrogel reduces impedance and spreads the RF energy emitted by the electrodes, thus avoiding the formation of hot spots and therefore excessive heating of the skin.

Excessive heating of the skin, it is to be remembered, is one of the limits that prevents other RF systems on the market from bringing the temperature of the fat to 45° C. and maintenance at that temperature.

The pad with hydrogel may be designed to be enriched also with active ingredients, pharmaceutical or cosmetic, slowly release, temperature controlled by the controller, as described in the present application. That is, the active ingredients could be encapsulated, and their release would take place only when a specific temperature level is reached for the purpose of the treatment.

FIGS. 8A through 8H illustrate the design of an applicator that may be RF only or RF combined with EMS, or even EMS only.

FIGS. 9A through 9H illustrate the design of an applicator that is a combination of RF and EMS.

The invention claimed is:

1. A method for evaluating effects of muscle stimulations on one or more body portions of a patient and treating the patient comprising:
   providing an applicator having one or more electromagnetic muscle stimulation (EMS) coils mounted on the applicator, the applicator further comprising an accelerometer, the accelerometer being capable of detecting a level of muscle contraction and release;
   providing a programmable controller to selectively activate the one or more EMS coils and control the operation of the accelerometer;
   positioning the applicator on one or more portions of the patient's body;
   after the applicator is positioned on the one or more portions of the patient's body, activating the one or more EMS coils, the accelerometer being configured to determine an the extent of muscle contraction and release due to the activation of the one or more EMS coils on the one or more portions of the patient's body on which the applicator is positioned;
   determining the portion of the one or more portions of the patient's body that obtains a highest desired muscle contractions; and
   providing treatment to the patient with the one or more EMS coils at the portion of the one or more portions that obtained the highest desired muscle contractions.

2. The method of claim 1, further comprising a step, prior to the determining step, of moving the applicator over portions of the patient's body to determine the portion of the one or more portions of the patient's body that obtains the highest desired muscle contractions.

3. The method of claim 1, further comprising, after positioning the applicator on the one or more portions of the patient's body, designating to the programmable controller that position to be a starting zero position.

4. An apparatus for evaluating effects of muscle stimulations on one or more body portions of a patient and treating the patient comprising:

an applicator having one or more electromagnetic muscle stimulation (EMS) coils mounted on the applicator, the applicator further comprising an accelerometer, the accelerometer being capable of detecting a level of muscle contraction and release;

a programmable controller to selectively activate the one or more EMS coils and control operation of the accelerometer;

the applicator being configured to be placed on one or more portions of the patient's body;

the programmable controller being configured to activate the one or more EMS coils;

the accelerometer being configured to determine an extent of muscle contraction and release due to the activation of the one or more EMS coils on the one or more portions of the patient's body on which the applicator is positioned;

the controller being configured to determine the portion of the one or more portions of the patient's body that obtains the highest desired muscle contractions; and the controller being configured to cause the providing of treatment to the patient with the one or more EMS coils at the portion of the one or more portions that obtained the highest desired muscle contractions.

5. The apparatus of claim 4, further comprising a step, prior to the controller being configured to determine the portion of the one or more portions of the patient's body that obtains the highest desired muscle contractions, of moving the applicator over portions of the patient's body to determine the portion of the one or more portions of the patient's body that obtains the highest desired muscle contractions.

6. The apparatus of claim 4, further comprising, after positioning the applicator on the one or more portions of the patient's body, designating to the programmable controller that position to be a zero starting zero position.

* * * * *